US012150726B2

(12) United States Patent
Luptak et al.

(10) Patent No.: US 12,150,726 B2
(45) Date of Patent: Nov. 26, 2024

(54) CONTROL SWITCH POSITION SENSING ACROSS A ROTATIONAL JOINT

(71) Applicant: Intuitive Surgical Operations, Inc., Sunnyvale, CA (US)

(72) Inventors: Brian Luptak, Santa Clara, CA (US); Matthew Cavalier, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 950 days.

(21) Appl. No.: 17/269,848

(22) PCT Filed: Aug. 21, 2019

(86) PCT No.: PCT/US2019/047565
§ 371 (c)(1),
(2) Date: Feb. 19, 2021

(87) PCT Pub. No.: WO2020/041513
PCT Pub. Date: Feb. 27, 2020

(65) Prior Publication Data
US 2021/0251707 A1 Aug. 19, 2021

Related U.S. Application Data

(60) Provisional application No. 62/721,467, filed on Aug. 22, 2018.

(51) Int. Cl.
A61B 34/37 (2016.01)
A61B 34/00 (2016.01)
(Continued)

(52) U.S. Cl.
CPC ............. A61B 34/37 (2016.02); A61B 34/35 (2016.02); A61B 34/74 (2016.02); A61B 90/06 (2016.02);
(Continued)

(58) Field of Classification Search
CPC ......... A61B 34/37; A61B 34/35; A61B 34/74; A61B 90/06; A61B 2090/061; A61B 2562/0223
See application file for complete search history.

(56) References Cited

U.S. PATENT DOCUMENTS 5,855,583 A    1/1999  Wang et al.
6,587,750 B2*  7/2003  Gerbi ................ A61B 34/70
                                              600/595
(Continued)

FOREIGN PATENT DOCUMENTS

CN        107848115 A      3/2018
WO   WO-2018112227 A2      6/2018

OTHER PUBLICATIONS

International Preliminary Report on Patentability for Application No. PCT/US2019/047565, mailed on Mar. 4, 2021, 07 pages.
(Continued)

Primary Examiner — Rina I Duda
(74) Attorney, Agent, or Firm — IP Spring

(57) ABSTRACT

Implementations relate to control switch position sensing across a rotational joint. In some implementations, a control input device includes a base member and a roll member rotatable about a central axis with respect to the base member in a roll degree of freedom. A switch contact portion is rotatable with the roll member and moveable to multiple positions in a switch degree of freedom. A first sensor element is coupled to and moveable with the switch contact portion and can be a passive element. A base sensor element is coupled to the base member and configured to sense a proximity of the first sensor element to the base sensor element, and to output a signal indicative of a current position of the switch contact portion in the switch degree of
(Continued)

freedom independently of a rotational orientation of the roll member in the roll degree of freedom.

20 Claims, 10 Drawing Sheets

(51) Int. Cl.
 *A61B 34/35* (2016.01)
 *A61B 90/00* (2016.01)
(52) U.S. Cl.
 CPC . *A61B 2090/061* (2016.02); *A61B 2562/0223* (2013.01)

(56) References Cited

U.S. PATENT DOCUMENTS

| | | | |
|---|---|---|---|
| 6,594,552 B1 * | 7/2003 | Nowlin | A61B 34/70 318/568.22 |
| 7,061,466 B1 | 6/2006 | Moore et al. | |
| 8,521,331 B2 * | 8/2013 | Itkowitz | A61B 34/37 606/1 |
| 8,543,240 B2 * | 9/2013 | Itkowitz | G06F 3/014 601/130 |
| 8,638,057 B2 | 1/2014 | Goldberg et al. | |
| 2003/0060927 A1 | 3/2003 | Gerbi et al. | |
| 2008/0046122 A1 | 2/2008 | Manzo et al. | |
| 2010/0080669 A1 | 4/2010 | Labonville et al. | |
| 2012/0051753 A1 * | 3/2012 | Labonville | A61B 34/74 398/140 |

OTHER PUBLICATIONS

International Search Report and Written Opinion for Application No. PCT/US2019/047565, mailed on Nov. 14, 2019, 9 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

CONTROL SWITCH POSITION SENSING ACROSS A ROTATIONAL JOINT

CROSS-REFERENCE TO RELATED APPLICATIONS

The present application is a U.S. National Phase application of International Patent Application No. PCT/US2019/047565, filed Aug. 21, 2019 and titled "Control Switch Position Sensing Across a Rotational Joint." which claims priority to U.S. Provisional Patent Application No. 62/721,467, filed Aug. 22, 2018 and titled "Control Switch Position Sensing Across a Rotational Joint," the entire contents of both of which are hereby incorporated by reference.

BACKGROUND

Controller mechanisms, e.g., control input devices, allow a user to control functions of various types of mechanisms and instruments. Teleoperated operations are one type of operation that can use control input devices. Teleoperated surgical devices, for example, can use various types of medical instruments to perform minimally invasive surgical procedures that reduce damage to healthy tissue of patients. The medical instruments can be connected to slave devices such as slave arms that can be manipulated to perform the surgical procedures. Control of the medical instruments at a slave device can be provided to an operator at one or more master control devices, e.g., at a remote operator terminal or station, and/or using a hand control device. Actuators of the slave device can be controlled by the master control device to cause motion or initiate another function of a medical instrument, camera, or other end effector at the slave device that interacts with the patient surgical site. In some examples, the master control device at the operator station can be physically manipulated by the operator in one or more degrees of freedom to control the end effector to be moved in coordination with the manipulation of the control device, e.g., to move in corresponding degrees of freedom at the operating site.

One of the degrees of freedom of a master control device can include a rotational degree of freedom of a handle of the master control device. For example, in some teleoperated systems, a master control device can include one or more grips that are pressed and/or rotated by the operator to control a corresponding motion of an end effector. For example, pincher grips on a master control device can provide a pinching motion that can control a similar pinching motion of forceps, tweezers, scissors, or other end effector instruments on a controlled slave device. Such grips on the master control device can be oriented to close along a central axis of the master control device, and they can be rotated about the central axis to command, for example, similar rotational motion of a slave instrument about an instrument axis. However, such rotational motion of a master control device may cause difficulties in providing data, power, and other signals to and from the rotating device portion to a base or grounded portions of the master control device. For example, control switches may be positioned on the rotating portion to allow a user to select various commands and functions during operation of the control system, and such control switches may be required to communicate states to non-rotating portions of the master control device while allowing the rotating portion to have continuously free and independent rotation.

SUMMARY

Implementations of the present application relate to control switch position sensing across a rotational joint. In some implementations, a control input device includes a base member and a roll member coupled to the base member and rotatable about a central axis with respect to the base member in a roll degree of freedom. A switch contact portion is coupled to the roll member and is rotatable with the roll member about the central axis in the roll degree of freedom. The switch contact portion is moveable to multiple positions in a switch degree of freedom with respect to the roll member. A first sensor element is coupled to the switch contact portion and is moveable with the switch contact portion in the switch degree of freedom and in the roll degree of freedom, where the first sensor element is a passive element configured to not receive electric signals. A base sensor element is coupled to the base member and configured to sense a proximity of the first sensor element to the base sensor element, where the base sensor element is configured to output a signal indicative of a current position of the switch contact portion in the switch degree of freedom independently of a rotational orientation of the roll member in the roll degree of freedom.

Various implementations and examples of the control input device are described. For example, in some implementations, the first sensor element is an unpowered sensor element. In some implementations, the first sensor element is a passive magnet and the base sensor element includes a Hall effect sensor. In some implementations, the passive magnet is coupled to the switch contact portion by an elongated link member. In some implementations, the passive magnet is a portion of a ring magnet. In some implementations, the base sensor element includes one or more optical detectors configured to detect a beam of electromagnetic energy reflected from the first sensor element. In some implementations, the base sensor element includes a sensor array having a plurality of sensors arranged at least partially concentrically about the central axis. In some examples, the base sensor element includes a sensor array having a plurality of Hall effect sensors arranged at least partially concentrically about the central axis. In some implementations, the signal indicative of the current position of the switch contact portion is also indicative of the rotational orientation of the roll member in the roll degree of freedom.

Some implementations further include a second switch contact portion moveable in a second switch degree of freedom, where the second switch contact portion is coupled to a second sensor element moveable with the second switch contact portion in the second switch degree of freedom and in the roll degree of freedom, and the second sensor element is a passive sensor element. In some examples, the first sensor element is a magnet having a first magnetic pole facing the base sensor element, and the second sensor element is a magnet having a second magnetic pole facing the base sensor element, the second magnetic pole having a polarity that is opposite to a polarity of the first magnetic pole. Some implementations further include a grip member coupled to the roll member and rotatable with the roll member about the central axis, where the grip member is rotatably coupled to the base member by a shaft extending through an axial passage formed in the roll member, the first sensor element is coupled to a link member, and the link member extends parallel to the shaft and is coupled to the switch contact portion. For example, some implementations further include an actuator coupled to the shaft and operative to output a linear force on the shaft along a longitudinal axis of the shaft, where the linear force causes a grip force to be applied via the shaft to the grip member in a grip degree of freedom, and the shaft is decoupled in rotation from the actuator about the longitudinal axis of the shaft.

In some implementations, a control input device includes a base member and a roll member coupled to the base member and rotatable about a central axis with respect to the base member in a roll degree of freedom. A switch contact portion is coupled to the roll member and is rotatable with the roll member about the central axis in the roll degree of freedom. The switch contact portion is moveable to multiple positions in a switch degree of freedom with respect to the roll member. A first sensor element is coupled to the switch contact portion and is moveable with the switch contact portion in the switch degree of freedom and in the roll degree of freedom. A base sensor element is coupled to the base member and configured to sense a proximity of the first sensor element to the base sensor element, where the base sensor element is arranged concentrically about the central axis, and the base sensor element is configured to output a signal indicative of a current position of the switch contact portion in the switch degree of freedom independently of a rotational orientation of the roll member in the roll degree of freedom.

Various implementations and examples of the control input device are described. For example, in some implementations, the base sensor element includes a plurality of individual sensor elements arranged concentrically about the central axis, and the first sensor element is coupled to a link member having a longitudinal axis parallel to the central axis, where the plurality of individual sensor elements are spaced concentrically about the central axis. In some implementations, at least a portion of the first sensor element is overlapping with at least one of the plurality of individual sensor elements along an axis parallel to the central axis at all positions of the first sensor element in the roll degree of freedom.

In some implementations, the base sensor element includes a substrate, the substrate including an aperture, where the plurality of individual sensor elements are positioned on the substrate, where the control input device further comprises a grip member coupled to the roll member and rotatable with the roll member about the central axis, where the grip member is rotatably coupled to a shaft extending through an axial passage formed in the roll member and extending through the aperture in the substrate. In some implementations, the base sensor element includes a plurality of individual sensor elements, where the first sensor element is a passive magnet and the plurality of individual sensor elements include a plurality of Hall effect sensors. In some implementations, the first sensor element and base sensor element include an optical emitter and an optical detector.

In some implementations, a method to sense a switch of a control input device includes receiving user input at the control input device that causes a switch to move to a position in a switch degree of freedom with respect to a roll member of the control input device, where the roll member is rotatable in a rotary degree of freedom about a central axis with respect to a base member coupled to the roll member. The method includes sensing the position of the control switch in the switch degree of freedom, where the sensing includes sensing a first sensor element with respect to a base sensor element, the first sensor element coupled to the roll member and the base sensor element coupled to the base member, where the base sensor element includes a plurality of sensors arranged at least partially concentrically about the central axis. The sensing of the switch includes determining the position of the switch in the switch degree of freedom based on an output signal from the plurality of sensors indicating a proximity of the first sensor element to the respective sensors of the plurality of sensors.

In some implementations, a control input device includes a base member and a roll member including a first end, a second end opposite the first end, and a central axis defined between the first and second ends. The roll member is rotatable about the central axis in a roll degree of freedom. A switch contact portion is coupled to the roll member and is rotatable with the roll member about the central axis in the roll degree of freedom, where the switch contact portion is moveable in a switch degree of freedom with respect to the roll member. The control input device includes a base sensor element of a distance sensor system, where the base sensor element coupled to the base. The control input device includes a first sensor element of the distance sensor system, where the first sensor element coupled to the switch contact portion. The first sensor element is rotatable with the roll member about the central axis in the roll degree of freedom and is moveable with the switch contact portion in the switch degree of freedom. The first sensor element is separated from the base sensor element by a variable distance that corresponds to positions of the switch contact portion in the switch degree of freedom. In various implementations, of the control input device, a signal is generated by the base sensor element, the signal including a parameter, where the parameter includes a value that corresponds to the variable distance that corresponds to positions of the switch contact portion in the switch degree of freedom. In some implementations, the value further corresponds to positions of the roll member about the central axis.

DETAILED DESCRIPTION

Figure 1:
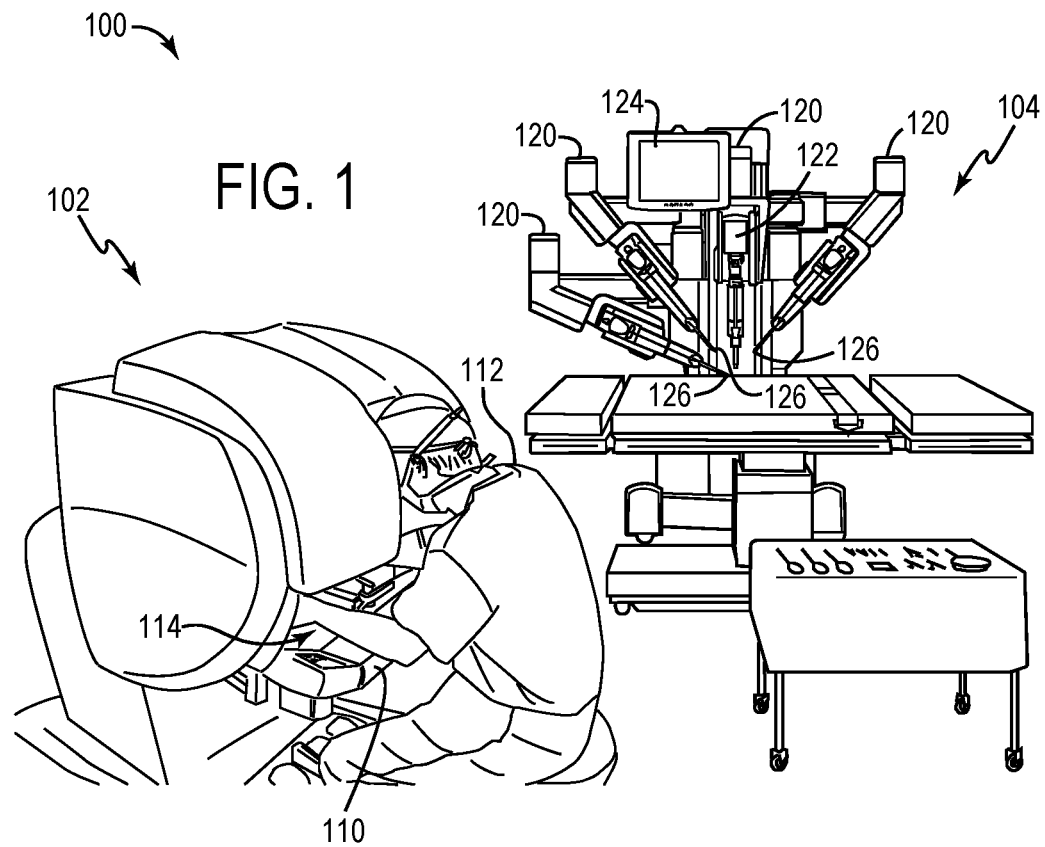
FIG. 1 is a diagrammatic illustration of an example implementation of a teleoperated surgical system which can be used with one or more features disclosed herein, according to some implementations.

One or more implementations described herein relate to sensing of positions of a control switch across a rotational joint of a control input device. In some implementations, a control input device includes a base member and a roll member rotatable about a central axis with respect to the base member in a roll degree of freedom, creating a rotational joint between base member and roll member. A switch contact portion is coupled to the roll member is moveable therewith. A first sensor element is coupled to the switch contact portion, and can be a passive element, e.g., it does not receive electric signals such as control signals or power, and is free to rotate with the roll member. A base sensor element is coupled to the base member and is configured to sense a proximity of the first sensor element to the base sensor element, and is configured to output one or more signals indicative of a current position of the switch contact portion in the switch degree of freedom independently of the rotational orientation of the roll member in the roll degree of freedom. Furthermore, the output signals can indicate the rotational orientation of the handle in the roll degree of freedom.

Various other features are also disclosed. For example, the first sensor element can be a magnet, which can be disc-shaped, partially ring-shaped, etc. The base sensor element can include one or more Hall effect sensors to sense the magnetic field of the magnet. For example, the base sensor element can be a sensor array that includes multiple sensors arranged concentrically about the central axis. The first sensor element can be attached at the end of a link member or plunger that extends parallel to the central axis, which allows a main shaft to be provided coincident with the central axis in the control input device and clear of any components of the switch mechanism. For example, such a shaft can be used to apply forces from an actuator to one or more grip members of the control input device that are contacted by a user's hand. Other types of sensors can be used, such as an optical emitter and detector and, e.g., reflecting a beam off of a reflective or patterned first sensor element of the switch mechanism.

In some implementations, the control input device includes a second switch moveable in its own switch degree of freedom. For example, a second switch contact portion can be coupled to a second sensor element moveable with the second switch contact portion. The base sensor element can detect the proximity of the second sensor element. In some examples, the presence of both sensor elements and the switch positions of both switches can be detected simultaneously by the base sensor element by distinguishing a detected characteristic of the first and second sensor elements. For example, the first and second sensor elements can be magnets having poles of opposite polarity facing the base sensor element, allowing the base sensor element to distinguish the magnetic fields of the first and second sensor elements.

Features described herein provide a control input device with several advantages. For example, multiple positions of a switch can be detected across a rotational joint of the control input device, e.g., across a rotation axis of a handle allowing continuous rotation of the handle with respect to a base member. A sensor element of a switch can be rotated with the handle and the proximity of the sensor element can be detected at any rotational position of the handle by a base sensor such as a sensor array. For example, the sensor array can sense the distance to the sensor array of the sensor element that orbits off the center axis during handle rotation. In some implementations, the use of compact switch elements and a base sensor array allows the distance of the sensor element to the center axis to easily scale. Furthermore, some implementations allow multiple switches of the handle to be distinguished and their positions to be simultaneously detected by the base sensor.

The base sensor remains stationary with respect to handle rotation, and can measure the position of the switch independently of the rotational position of the handle, e.g., independently of the roll position of the sensor element. For example, the base sensor can be an active circuit, e.g., send signals to other controller components and receive power. The detectable sensor element of the switch can be implemented using passive components (positioned on the roll side of the continuous rotary joint) and thus the sensor element and switch mechanism need not communicate any signals across the rotating joint, including data and power.

Such features are advantageous over previous methods that required power and data to be transmitted across a rotary joint or continuous rotating axis, e.g., using optical transmission or other methods, which can be expensive, difficult to assemble, and encompasses valuable space along the area of a central axis of a control input device. Described implementations of switch mechanisms allow the center axis of the handle to be left unoccupied and available for useful drive-train components. The switch mechanism and detection mechanism implementations described herein are compact, robust, and inexpensive.

The terms "center," "parallel," "perpendicular," "aligned," or particular measurements in degrees, Hertz, or other units as used herein need not be exact and can include typical engineering tolerances.

FIG. 1 is a diagrammatic illustration of an example teleoperated surgical system 100 which can be used with one or more features disclosed herein. Other types of control systems and/or master-slave systems can be used in other implementations involving described features. Teleoperated surgical system 100 includes a master control workstation (e.g., surgeon's console) 102 and a manipulator slave device 104.

In this example, the master control workstation (e.g., surgeon's console) 102 includes a viewer 213 (shown in FIG. 2) where an image of a worksite is displayed during an operating procedure using the system 100. For example, the image can be displayed by a display device such as one or more display screens, depict a surgical site during a surgical procedure. A support 110 is provided on which a user 112, e.g., an operator such as a surgeon, can rest his or her forearms while gripping two master controllers 210 and 212 (shown in FIG. 2), one in each hand. The master controllers are positioned in a workspace 114 disposed inwardly beyond the support 110. When using the workstation 102, the user 112 can sit in a chair in front of the workstation, position his or her eyes in front of the viewer and grip the master controllers, one in each hand, while resting his or her forearms on the support 110. Additional details are described below with reference to FIG. 2.

A slave device 104 is also included in the teleoperated system 100. For example, slave device 104 can be a manipulator slave device in this example, or can alternatively be a different type of slave device. During a surgical procedure, the slave device 104 can be positioned close to a patient (or simulated patient) for surgery, where it can remain stationary until a particular surgical procedure or stage of a procedure is completed. Slave device 104 can include one or more manipulator arm assemblies 120. In some examples, one or more of the arm assemblies 120 can be configured to hold an image capturing device, e.g., an endoscope 122, which can provide captured images of a portion of the surgical site. In some implementations, the captured images can be transmitted to the viewer of the workstation 102 and/or transmitted to one or more other displays, e.g., a display 124 coupled to the slave device 104. In some examples, each of the other arm assemblies 120 may include a surgical tool 126. Each surgical tool can include a surgical end effector, e.g., for treating tissue of the patient. For example, the end effector can include one or more motors or other actuators that operate associated features of the end effector, such as the pitch, yaw, and/or roll of the end effector, opening jaws or moving a blade of the end effector, the output of material transported through a connecting tube (e.g., liquid or other fluids), suction forces, and/or any of a multiple of other end effector functions. One example of a surgical manipulator arm is a da Vinci® surgical system instrument manipulator arm available from Intuitive Surgical, Inc. of Sunnyvale, Calif.

In this example, the arm assemblies 120 can be caused to move and articulate the surgical tools 126 in response to manipulation of the master controllers 210 and 212 at the workstation 102 by the user 112, e.g., so that the user 112 can direct surgical procedures at internal surgical sites through minimally invasive surgical apertures. For example, one or more actuators coupled to the arm assemblies 120 can output force to cause links or other portions of the arm assemblies to move in particular degrees of freedom in response to control signals received from the workstation 102. For example, movement of an arm and end effector in one or more degrees of freedom can correspond to movement in one or more degrees of freedom of an associated master controller handle by a user. The workstation 102 can be used within a room (e.g., an operating room) with the slave device 104 or can be positioned more remotely from the slave device 102, e.g., at a different location than the slave device.

Some implementations of the teleoperated system 100 can provide different modes of operation. In some examples, in a non-controlling mode (e.g., safe mode) of the teleoperated system 100, the controlled motion of the manipulator slave device 104 is disconnected from the master controllers of the workstation 102 in disconnected configuration, such that movement and other manipulation of the master controls does not cause motion of the manipulator slave device 104. In a controlling mode of the teleoperated system (e.g., following mode), motion of the manipulator slave device 104 can be controlled by the master controls 210 and 212 of the workstation 102 such that movement and other manipulation of the master controllers causes motion of the manipulator slave device 104, e.g., during a surgical procedure.

Some implementations can be or include a teleoperated medical system such as a da Vinci® Surgical System (e.g., a Model IS3000 or IS4000, marketed as the da Vinci Si® or da Vinci Xi® Surgical System), commercialized by Intuitive Surgical, Inc. of Sunnyvale, California. However, features disclosed herein may be implemented in various ways, including teleoperated and, if applicable, non-teleoperated (e.g., locally-controlled) implementations. Implementations on da Vinci® Surgical Systems are merely exemplary and are not to be considered as limiting the scope of the features disclosed herein. For example, different types of teleoperated systems having slave devices at worksites can make use of actuated controlled features described herein. Other, non-teleoperated systems can also use one or more described features, e.g., various types of control systems and devices, peripherals, etc.

In some implementations, a controlled slave device can be a virtual representation of device, e.g., presented in a graphical simulation provided by a computing device coupled to the teleoperated system 100. For example, a user can manipulate the master controls 210 and 212 of the workstation 102 to control a displayed representation of an end effector in virtual space of the simulation, similarly as if the end effector were a physical object coupled to a physical slave device.

In various implementations, other types of control systems and computer-assisted teleoperated systems can be used with one or more control and sensing features described herein, in addition to surgical systems. Teleoperated systems can include controlled slave devices of various forms. For example, submersibles, bomb disposal units, industrial applications, applications in hostile environments and worksites (e.g., due to weather, temperature, pressure, radiation, or other conditions), general robotics applications, and/or remote-control applications (e.g., remote controlled vehicle or device providing a first-person camera view), may utilize teleoperated systems that include slave devices for sensory transmission (conveyed visual, auditory, etc. experience), manipulation of work pieces or other physical tasks, etc., and may use mechanically grounded and/or ungrounded master controllers to remotely control the slave devices. Any such teleoperated systems, and other systems, can be used with the various hand controller sensing features described herein.

Figure 2:
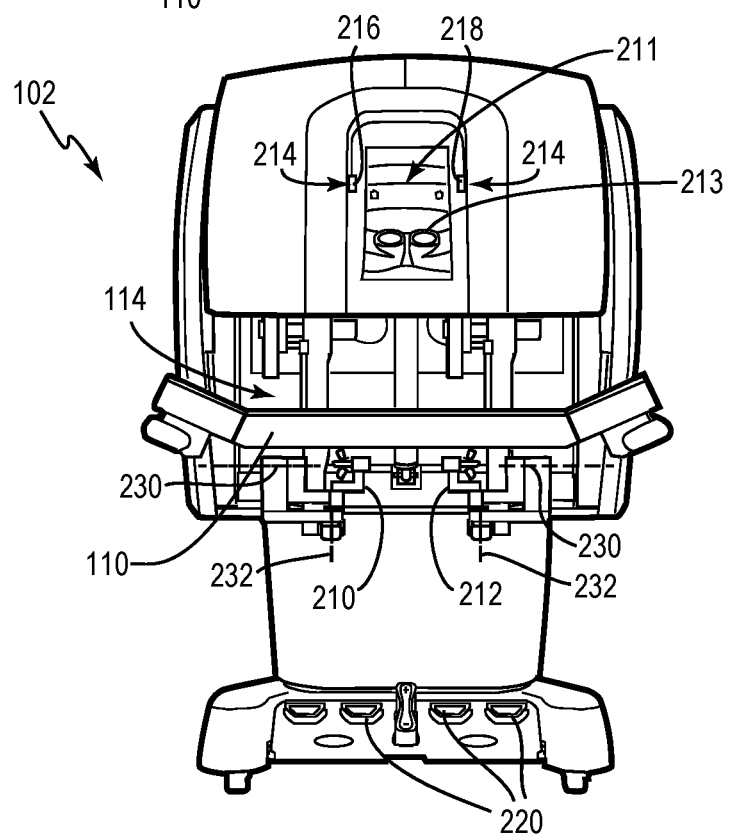
FIG. 2 is a front elevational view of an example master control workstation as shown in FIG. 1, according to some implementations.

FIG. 2 is a front elevational view of an example master control workstation 102 as described above for FIG. 1. Master control workstation 102 includes a viewer 213, where an image of a worksite can be displayed during a procedure using the teleoperated system 100. For example, images depicting a surgical site can be displayed during a surgical procedure. The viewer 213 can be positioned within a viewing recess 211 in which the user can position his or her head to view images displayed by the viewer 213. When using the workstation 102, the user 112 can sit in a chair in front of the workstation and position his or her head within the recess 211 such that his or her eyes are positioned in front of the viewer 213.

In some implementations, one or more user presence sensors 214 can be positioned at one or more locations of the master control workstation 102 to detect the presence of a user located next to or near to the workstation 102. In this example, the user presence sensors 214 can sense a presence of a user's head within the recess 211. For example, an optical sensor can be used for a presence sensor, where the optical sensor includes an emitter 216 and a detector 218. A beam of infrared or other wavelength of light is emitted from one side of the recess 211 by the emitter 216, and the beam is detected on the other side of the recess by the detector 218. If the beam is interrupted from detection by the detector, the system determines that a user's head is within the recess and that the user is in a proper position to use the master controllers of the master control workstation 102. Additional or alternative types of presence sensors can be used in various implementations.

Two master controllers 210 and 212 are provided for user manipulation. In some implementations, each master controller 210 and 212 can be configured to control motion and functions an associated arm assembly 120 of the slave device 104. For example, a master controller 210 or 212 can be moved in a plurality of degrees of freedom to move a corresponding end effector of the slave device 104 in corresponding degrees of freedom. The master controllers 210 and 212 are positioned in workspace 114 disposed inwardly beyond the support 110. For example, a user 112 can rest his or her forearms while gripping the two master controllers 210, 212, with one controller in each hand. The user also positions his or her head within the viewing recess 211 to view the viewer 213 as described above while manipulating the master controllers 210 and 212. Various examples of portions of control input devices that can be used as master controllers 210 and 212 are described below.

Some implementations of workstation 102 can include one or more foot controls 220 positioned below the master controls 210 and 212. The foot controls 220 can be depressed, slid, and/or otherwise manipulated by a user's feet to input various commands to the teleoperated system while the user is sitting at the master control workstation 102.

Figure 3:
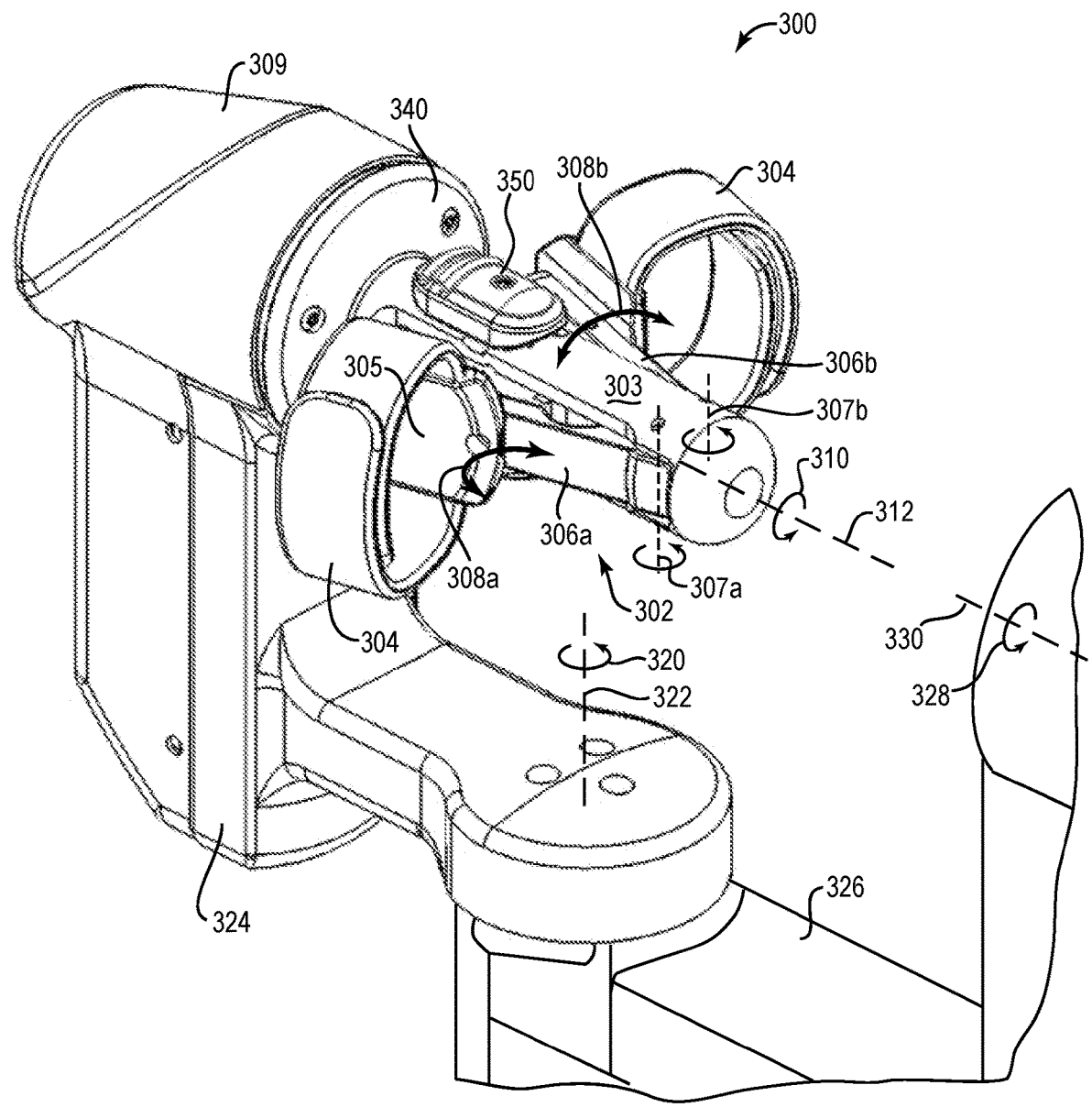
FIG. 3 is a perspective view of an example portion of a control input device which can include one or more features described herein, according to some implementations.

FIG. 3 is a perspective view of an example controller portion 300 of a control input device which can include one or more features described herein. In some implementations, controller portion 300 can be used as a portion of an input control device that is a master controller 210 or 212 as described above with reference to FIGS. 1 and 2, or portion 300 can be included in a different control device. In some implementations, the controller portion 300 includes one or more gimbal mechanisms.

Controller portion 300 includes a handle 302 which is contacted by a user to manipulate the control input device. In this example, the handle 302 includes two grips that each include a finger loop 304 and a grip member 306 (grip members 306a and 306b). The two grip members 306 are positioned on opposite sides of a central portion 303 of the handle 302, where the grip members 306 can be grasped, held, or otherwise contacted by a user's fingers. Each finger loop 304 is attached to a respective grip member 306 and can be used to secure a user's fingers to the associated grip member 306. In this example, finger contacts 305 can be connected or formed at the unconnected end of the grip members 306a and 306b to provide surfaces to contact the user's fingers. The user may also contact other portions of handle 302 while grasping the grip members 306.

Each grip member 306 and finger loop 304 can be moved in an associated degree of freedom 308 (e.g., 308a and 308b). In some examples, the grip members 306a and 306b are each coupled to the central portion 303 of the handle 302 at respective rotational couplings, allowing rotational movement of the grip members about grip axes 307a and 307b, respectively, with respect to the central portion 303. Each grip member 306a and 306b can be moved in an associated degree of freedom 308a about axis 307a and degree of freedom 308b about axis 307b, respectively, e.g., by a user contacting the grip members. For example, in some implementations the grip members 306a and 306b can be moved simultaneously in a pincher-type of movement (e.g., toward or away from each other). In various implementations, a single grip member 306 and finger loop 304 can be provided, or only one of the grip members 306 can be moved in the degree of freedom 308 while the other grip member 306 can be fixed with reference to the handle 302. For example, the positions of grip members 306a and 306b in their degrees of freedom can control corresponding rotational positions of an end effector or component thereof.

One or more sensors (not shown) can be coupled to the handle 302 and/or other components of the controller portion 300 and can detect the positions of the grip members 306a and 306b in their degrees of freedom 308. The sensors can send signals describing sensed positions and/or motions to one or more control circuits of the teleoperated system 100. In some modes or implementations, the control circuits can provide control signals to a slave device, e.g., slave device 104. For example, the positions of the grip members 306a and 306b in degrees of freedom 308a and 308b can be used to control any of various degrees of freedom of an end effector of the slave device 104, some examples of which are described herein.

Various implementations of the controller 300 can provide one or more active actuators (e.g., motors, voice coils, etc.) to output active forces on the grip members 306 in the degrees of freedom 308. For example, a sensor and/or actuator can be housed in central portion 303 or in housing 309 and coupled to the grip members 306 by a transmission. Some implementations can provide one or more passive actuators (e.g., brakes) or springs between the grip members 306 and the central portion 303 of the handle 302 to provide resistance in particular directions of the grips (e.g., movement in directions toward each other in degree of freedom 308). Some examples of actuators and transmission are described below with respect to FIG. 11.

Handle 302 is additionally provided with a rotational degree of freedom 310 about a roll axis 312 defined between a first end and second end of the handle 302. The roll axis 312 is a longitudinal axis in this example that extends approximately along the center of the central portion 303 of handle 302. Handle 302 can be rotated about axis 312 with respect to a base member of the controller portion 300, such as housing 309, thus creating a rotational joint between handle 302 and the base member. For example, a user can rotate the grip members 306 and central portion 303 as a single unit around the axis 312, with respect to housing 309, to provide control of a slave device, such as an end effector of the slave device 104 or other element of the slave device.

One or more sensors (not shown) can be coupled to the handle 302 to detect the rotation and/or position of the handle 302 in the rotational degree of freedom 310. For example, the sensor can send signals describing the position to control circuits of the teleoperated system 100 which can provide control signals to the slave device 104 similarly as described above. For example, rotation of handle 302 in degree of freedom 310 can control a particular degree of freedom of an end effector of the slave device that is different than a slave degree of freedom controlled by degree of freedom 308 of the grip members 306.

Some implementations of the controller portion 300 can provide one or more actuators to output forces on the handle 302 (including grip members 306 and finger loops 304) in the rotational degree of freedom 310. For example, a sensor and/or actuator can be housed in housing 309 and coupled to the handle 302 by a shaft extending through the central portion 303 of the handle 302.

In various implementations, the handle 302 can be provided with additional degrees of freedom. For example, a rotational degree of freedom 320 about a yaw axis 322 can be provided to the handle 302 at a rotational coupling between an elbow shaped link 324 and a link 326, where the elbow shaped link 324 is coupled to the handle 302 (e.g., at housing 309). In this example, yaw axis 322 intersects and is orthogonal to the roll axis 312. For example, yaw axis 322 can be similar to axis 232 shown in FIG. 2. Additional degrees of freedom can similarly be provided. For example, link 326 can be elbow-shaped and a rotational coupling can be provided between the other end of link 326 and another link (not shown). A rotational degree of freedom 328 about an axis 330 can be provided to the handle 302 at the rotational coupling. For example, axis 330 can be similar to axis 230 shown in FIG. 2. In some examples, the controller portion 300 can allow movement of the handle 302 within the workspace 114 of the master control workstation 102 with a plurality of degrees of freedom, e.g., six degrees of freedom including three rotational degrees of freedom and three translational degrees of freedom. One or more additional degrees of freedom can be sensed and/or actuated similarly as described above for the degrees of freedom 308 and 310. In some implementations, each additional degree of freedom of the handle 302 can control a different slave degree of freedom (or other motion) of an end effector of the slave device 104.

In the described example, handle 302 includes one or more control switches 350, e.g., coupled to the central portion 303 or to mechanisms within central portion 303. For example, two control switches 350 can be positioned on opposite sides of axis 312, and/or additional control switches can be provided. In some examples, a control switch 350 has a portion that can slide parallel to the axis 312, e.g., as directed by a user's finger, or the control switch portion can be depressed. In some implementations, the control switch 350 can be moved to various positions to provide particular command signals, e.g., to select functions, options, or modes of the control console and/or master controller (e.g., a controlling mode or non-controlling mode as described herein), to command a slave device or other system in communication with the master controller, etc.

In some implementations, one or more of the control switches 350 can be implemented as a button (e.g., depressed in a direction, such as perpendicular to the axis 312 or other direction), a rotary dial, a switch that moves perpendicular to the axis 312, or other type of input control.

In some example implementations, control switch 350 is a contact portion of a switch mechanism that is moved based on manipulation by a user and is sensed by a switch sensor. For example, a switch sensor can coupled to a plate 340, where the plate 340 is rigidly coupled to the housing 309 and is stationary with respect to rotation of the handle 302 about axis 312. When the switch 350 is activated by the user, e.g., slid by a user parallel to axis 312, a switch element is moved into a range sensed by the sensor. Example mechanisms and switch operation are described in greater detail below. Other types of sensors can alternatively be used, such as optical sensors, mechanical switches, etc.

One or more features described herein can be used with other types of master controllers. For example, ungrounded master controllers can be used, which are free to move in space and disconnected from ground. In some examples, one or more handles similar to handle 302 and/or grip members 306 can be coupled to a mechanism worn on a user's hand and which is ungrounded, allowing the user to move grips freely in space. In some examples, the positions of the grips relative to each other and/or to other portions of the handle can be sensed by a mechanism coupling the grips together and constraining their motion relative to each other. Some implementations can use glove structures worn by a user's hand. Furthermore, some implementations can use sensors coupled to other structures to sense the grips within space, e.g., using video cameras or other sensors that can detect motion in 3D space. Some examples of ungrounded master controllers are described in U.S. Pat. Nos. 8,543,240 B2 (filed Sep. 21, 2010) and 8,521,331 B2 (filed Nov. 13, 2008), both incorporated herein by reference in their entireties.

Figure 4:
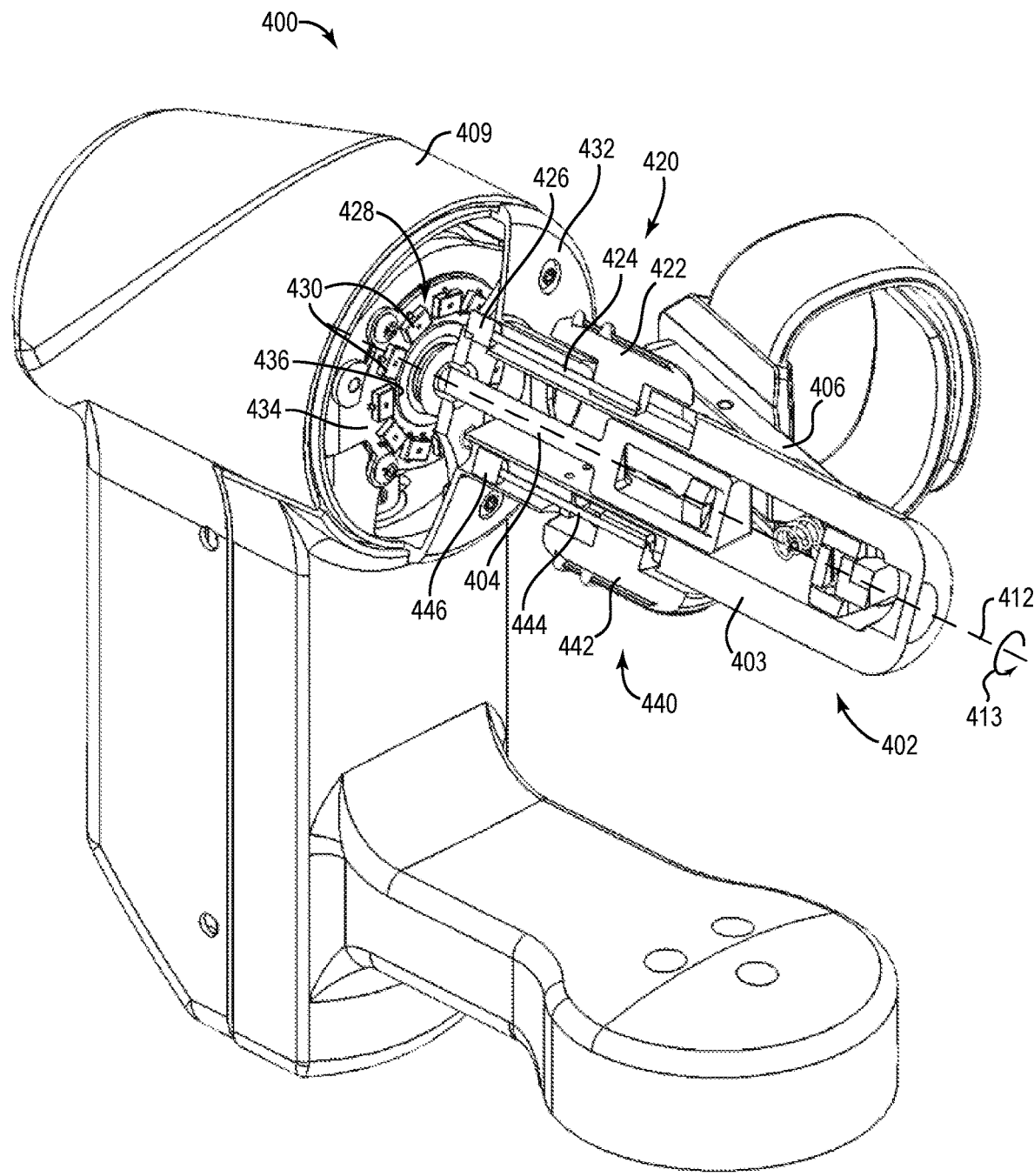
FIG. 4 is a perspective view of an example portion of a control input device including an example implementation of a switch mechanism and sensor for a control switch, according to some implementations.

FIG. 4 is a perspective partial cross-sectional view of an example implementation of a controller portion 400 of a control input device including an example implementation of a sensor system for a control switch. In some implementations, the controller portion 400 can be implemented as the control portion 300 described above with respect to FIG. 3, or can be included in a different input control device.

Controller portion 400 includes a handle 402 (shown in cross section) and base member, similar to handle 302 as described for FIG. 3. Handle 402 includes a first end, a second end opposite the first end, and a central axis 412 defined between the first and second ends. Handle 402 (e.g., a roll member) can be rotated about central axis 412 in a roll degree of freedom 413 with respect to the base member that includes a housing 409, thus creating a rotational joint between handle 402 and the base member. For example, in some implementations, handle 402 can include the grip members 406 similarly as grip members 306 of FIG. 3 (only one grip member 406 is shown in FIG. 4). In some implementations, an actuator (e.g., motor) can be used to drive rotation of the handle 402 about central axis 412, some examples of which are described below. One or more sensors can be coupled to the controller portion 400 and detect the roll (rotary) orientation of the handle 402 about axis 412. The sensors can send signals describing sensed positions, orientations, and/or motion to control circuits of the teleoperated system 100. In some modes or implementations, the control circuits can provide control signals to the slave device 104.

In some implementations, handle 402 can include a main shaft 404 that is connected to and drives grip members 406. In some implementations, main shaft 404 can be translated along axis 412 by an actuator (e.g., motor) to cause force in the degrees of freedom of the grip members 406. Some examples of an actuator and transmission driving a shaft are described below. In some implementations, one or more sensors can be coupled to the shaft 404 or to the actuator to detect linear movement of the shaft 404 and provide sensor signals to control circuits similarly as for the roll sensor.

In some implementations, the controller portion includes at least a portion of a distance sensor system that can be used to detect switch positions of a control switch. The distance sensor system can include a base sensor element and a first sensor element, examples of which are described herein. For example, the first sensor element can be included in a switch mechanism and/or coupled to a switch contact portion. A signal generated by the base sensor element can include a parameter, and the parameter can include a value that corresponds to a variable distance. The variable distance corresponds to positions of a switch contact portion in a switch degree of freedom. In some implementations, the value further corresponds to rotational orientations of the roll member about the central axis.

In the described implementation, handle 402 includes a switch mechanism 420 that is coupled to the central portion 403 of the handle 402, which in some examples can be used for the control switch 350 of FIG. 3. Switch mechanism 420 includes a switch contact portion 422 that is configured to translate or slide in both directions in a switch degree of freedom along a linear axis parallel to the longitudinal axis 412. For example, the switch contact portion 422 can contact a central portion 403 of the controller portion 400 and can translate with respect to the central portion 403. The switch contact portion 422 is configured to be engaged by a finger of an operating hand of the user and moved in the switch degree of freedom.

In some implementations, the switch contact portion 422 can be moved to any of multiple positions in the switch degree of freedom. In some example implementations, the switch contact portion 422 can be moved a range of about 5 millimeters in its linear degree of freedom, or can be moved within other ranges in other implementations. In various examples, two switch positions, three switch positions, or additional switch positions are provided. In some implementations, mechanical detents can be provided in a groove or other pathway of the switch contact portion 422 (or plunger 424) to mechanically restrain the switch contact portion to particular switch positions, and/or to provide haptic feedback to a user's finger that contacts the switch contact portion 422 to indicate the particular switch positions.

A switch sensing extension is coupled to the switch contact portion 422. In this example, the extension is an elongated link member, e.g., a plunger 424. Plunger 424 has a longitudinal axis that extends parallel to the longitudinal axis 412 from the switch contact portion 422 toward and/or through a plate 432, e.g., away from the central portion 403 and the grip members 406. A switch sensor element 426 is coupled to the plunger 424. Sensor element 426 is a passive sensed element, such as a magnet, in the described implementation, but can be other types of sensor elements in other implementations. The plunger 424 and element 426 move linearly parallel to axis 412 in correspondence with the movement of the switch contact portion 422.

In this example, element 426 has a planar surface that faces opposite to the switch contact portion 422 of the switch mechanism 420. In some implementations, element 426 can have a larger area or dimension extending perpendicularly to the longitudinal axis 412 than its other dimensions. Further examples of element 426 are described below with reference to FIGS. 5 and 6.

In some implementations, element 426 is disc-shaped, or can alternatively be rectangular or have a different shape. In some implementations, element 426 can be a neodymium magnet having a magnetic field strength that allows the element 426 to be spaced from a sensor array (described below) while allowing the sensors of the sensor array to sense the magnet. Other types of magnets can be used in other implementations.

A base sensor element is coupled to a base member of the controller (e.g., housing 409 or link attached thereto) and is configured to sense the sensor element 426. In this example, the base sensor element is a sensor array 428. Sensor array 428 is coupled to the housing 409 of the controller portion 400. In this example, a member or substrate 434 is coupled to the base member and provides a surface perpendicular to the longitudinal axis 412, where the surface extends radially about the longitudinal axis 412. In some examples, a central aperture 436 is provided in the center of base member 434 and sensor array 428 to allow the main shaft 404 to extend through the base member 434 and the sensor array 428.

In the described implementation, a plurality of sensor array elements 430 of the sensor array 428 are arranged on the surface of substrate 434 (or parallel to the surface of member 434), where the sensor array elements 430 can be arranged radially around the longitudinal axis 412. The sensor array elements are thus coupled to the housing 409 and do not rotate about axis 412 with the handle 402 and switch mechanism 420, e.g., remain stationary with respect to the handle rotation. One or more sensor array elements 430 can sense a proximity (e.g., presence) of the sensor element 426. For example, array elements 430 can detect the sensor element 426 based on the current linear position of the element 426 along an axis parallel to axis 412 and based on the current rotational position of the element 426 about axis 412.

The sensor array outputs one or more signals indicative of the position of the switch mechanism 420 (including switch contact portion 422) in its switch degree of freedom. For example, each sensor array element 430 can produce a sensor signal (e.g., a voltage signal) that indicates a proximity of the sensor element 426, which can be used to determine the distance between the element 426 and the sensor array element as described herein. The sensor signal can be sent to a control system, e.g., via wires in the housing 409 or wirelessly in some implementations.

For example, if element 426 is a magnet, each sensor array element 430 can sense the magnetic strength of the magnet 426 at different distances of the magnet to that sensor array element 430 (when the magnet 426 is positioned within a sensing range of the sensor array element), and thus the sensor array 428 can sense the distance of the magnet 426 linearly along an axis parallel to axis 412. The sensed distance of the magnet 426 to the sensor array 428 can be used to determine the switch position of the switch mechanism 420 in its linear degree of freedom.

The switch mechanism 420, including switch contact portion 422, plunger 424, and sensor element 426, are rotated about axis 412 as the handle 402 is rotated about axis 412 in the rotational degree of freedom 413 of the handle 402. The element 426 is rotated with respect to the sensor array elements 430 which are coupled to the housing 409. If the switch contact portion 422 and element 426 are maintained at a constant linear (switch) position along axis 412, the element 426 passes within the same distance of each sensor array element 430 as the element 426 is rotated throughout the range of the roll degree of freedom.

In this example, eleven sensor array elements 430 are positioned approximately regularly about the longitudinal axis 412, such that the sensor element 426 is always sensed by at least one sensor array element 430 regardless of the position of the element 426 with respect to the sensor array elements 430 about axis 412. For example, the sensor element 426 can be continuously sensed by at least one sensor array element 430 independently of the rotational orientation of the handle 402 in the roll degree of freedom.

In some implementations, the sensor array 428 can be provided with an amount of array elements 430 to allow multiple array elements 430 to sense the sensor element 426. Such redundant detection by multiple array elements 430 can be used to perform error checking to detect whether any of those array elements is malfunctioning, for example. Furthermore, multiple array elements can allow the axial travel of the sensor element 426 (along axis 412) to be differentiated from the sensor element rotating about axis 412, since both of these movements can provide a decrease in strength of detection by the array elements 430 (e.g., an increasing air gap between a magnetic sensor element 426 and a Hall effect sensor 430). In general, the sensor array 428 can include a density of array elements 430 to allow checking of errors between array elements 130, and to differentiate such axial movement and rotational movement.

In this example, up to three array elements 430 can sense the sensor element 426 at the same time (e.g., due to the size of the magnetic field of a magnetic sensor element 426). In some examples, each sensor array element 430 can have a radial length that is approximately 25 degrees, or alternatively can have other sizes. Other amounts of sensor array elements, as well as different radial lengths, sensing areas, etc. of the array elements, can be used. In some implementations, an odd number of evenly-spaced sensor array elements 430 can increase the sensitivity of sensing radial rotation of the handle 402.

In the described implementations, sensor array elements 430 can be Hall effect sensors. Such a sensor can sense the amount of distance between the sensor and a magnetic element 426. Each Hall effect element 430 can detect the magnet 426 even when these elements are not directly overlapping in dimension parallel to the axis 412, since the magnetic field from magnet 426 extends further than the magnet itself. Each sensor array element 430 can produce a sensor signal (e.g., a voltage signal) that indicates a strength of a magnetic field strength sensed from magnet 426, and which can be used to determine the distance between the element 426 and the sensor array element. In other implementations, other types of sensors can be used, as described below.

In some implementations, the sensor array 428 can be provided on a substrate 434 that is a printed circuit board (PCB). For example, for a sensor array 428 having Hall effect sensors, a PCB can include a ferritic steel backing that shields the Halls effect sensors and shunts the flux to be stronger at the faces of the sensor array elements 430 facing the sensor element 426 (and facing sensor element 446 described below).

Using multiple sensor array elements 430 arranged about the axis 412 also allows the rotational position of the switch mechanism 420 to be sensed about the central axis 412. For example, at least two of the sensor array elements 430 (e.g., approximately three in some implementations) can sense the presence of the element 426 at any time, allowing an approximate radial position of the element 426 to be determined as described in greater detail below.

When using a magnetic element 426, the movement of the element 426 between two sensor array elements 430 is distinguishable by the sensor array 428 from a movement of the element 426 from a point closer to the sensor array 428 to a point further away from the sensor array in a direction parallel to the axis 412. Both of these movements cause a reduction in magnetic strength sensed by the sensor array 428. A sufficient number of sensor array elements 430 arranged radially about the axis 412 allows the element 426 to always be sensed by at least two sensors of the array 428 at any time, thus allowing radial movement of the element 426 to be distinguished from the linear movement.

The sensor array 428 can be connected to power wires and/or control signal wires that are routed to a power source (not shown) and the control circuits or other components of the controller portion 400. Since the sensor array 428 does not rotate with the handle 402, it can be connected to the housing 409 of the controller portion 400 that is stationary with respect to the rotation of handle 402. In contrast, the element 426 rotates with the handle 402, and does not receive or send any electric signals (e.g., data and/or power signals) related to sensing. For example, the element 426 can be an unpowered sensor element. In some examples, element 426 can be a passive sensor element that does not receive or require power and data signal connections that could otherwise constrain or limit rotation of handle 402, and/or that could otherwise require use of additional routing and communication components in the controller portion 400 (e.g., harness, optical communication of signals, etc.).

In some implementations, a second switch mechanism 440 is provided in handle 402, including a second switch contact portion 442, a second plunger 444, and a second sensor element 446. In the described implementation, the second switch mechanism 440 is positioned on the opposite side of handle 402 from the switch mechanism 420. Similarly to switch mechanism 420, switch contact portion 442 is configured to slide in both directions in a second switch degree of freedom along a linear axis parallel to the longitudinal axis 412 of the controller portion 400. In some implementations, the switch contact portion 440 can be moved to any of multiple positions in the second switch degree of freedom. For example, the second switch contact portion 440 can contact central portion 403 of the controller portion 400 and can translate with respect to the central portion 403.

A second switch sensing extension is coupled to the second switch contact portion 442, e.g., a second elongated link member such as second plunger 444. Second plunger 444 extends parallel to the longitudinal axis 412 from the second switch contact portion 442 toward and/or through the plate 432. Second sensor element 446 (e.g., switch sensor element 446) is coupled to the second plunger 444. In some examples, sensor element 446 can be a magnet similarly as described for element 426. The second plunger 444 and second element 446 move linearly parallel to axis 412 in correspondence with the movement of the second switch contact portion 442.

In this example, sensor element 446 can have a shape, surface, and orientation similar to sensor element 426. Sensor element 446 faces the sensor array 428 similarly to sensor element 426, except at a position on the opposite side of longitudinal axis 412. In an example similar to that of element 426, one or more sensor array elements 430 of the sensor array 428 can sense the proximity (e.g., presence) of the sensor element 446. For example, each sensor element 430 can sense the distance of the sensor element 446 to that respective sensor array element when that sensor array element is positioned within a particular sensing distance range of the sensor element 446.

In some implementations, the proximity (e.g., presence) of both switch mechanisms 426 and 446 can be detected simultaneously by the sensor array 428 by distinguishing the presence of the first and second sensor elements. For example, the first sensor element 426 can provide a different detectable characteristic than the second sensor element 446. In some examples, the different characteristic can be a physical characteristic, e.g., a different magnetic field, electric field, physical shape, color, surface angle (for reflection of an optical beam), or other characteristic.

For example, sensor elements 426 and 446 can be magnetic. Sensor element 446 can be positioned such that it is facing the sensor array 428 with a magnetic pole that is opposite to the pole of element 426 that faces the sensor array 428. This allows the sensor array 428 to sense a different respective magnetic field from each magnet 426 and 446, and allows the output of the sensor array 428 to simultaneously indicate independent position and motion of each of the sensor elements 426 and 446.

The second switch contact portion 442, second plunger 444, and second sensor element 446 are rotated about axis 412 as the handle 402 is rotated about axis 412 in the rotational degree of freedom 413 of the handle 402. The sensor element 446 is rotated with respect to the sensor array elements 430 which are coupled to the housing 409. If the switch contact portion 442 and sensor element 446 are maintained at a constant linear position along axis 412, the sensor element 446 passes within the same distance of each sensor array element 430 as the sensor element 446 is rotated throughout the range of its circular degree of freedom. With multiple sensor array elements 430 being positioned approximately regularly about the longitudinal axis 412, both the first element 426 and the second element 446 are continuously sensed by at least one sensor array element 430 of the sensor array 428 regardless of the position of the element 426 and element 446 with respect to the sensor array elements 430 about axis 412. For example, both sensor elements 426 and 446 can be continuously sensed by two or more sensor array elements 430 independently of the rotational orientation of the handle 402 in the roll degree of freedom. Similarly as described for element 426, in this example, the sensor element 446 is passive, e.g., does not receive or send any electric signals (e.g., data and power signals) related to sensing. For example, element 446 does not require power and data signal connections.

In this example, the switch mechanisms 420 and 440 and the sensor array 428 are configured to enable sensing of the positions of the switch mechanisms in their switch degrees of freedom using components that are arranged about the main shaft 404 without interfering with the shaft 404. The switch mechanisms 420 and 440 include plungers 424 and 444 that extend parallel to the shaft 404 and axis 412, allowing the sensor elements 426 and 446 to move in proximity to the sensor array 428 that is not coupled to the rotating handle 402. Such an arrangement allows the main shaft 404 to be driven along axis 412 by an actuator to apply forces to the grip members 406, without interference from components used for sensing the positions of the switch mechanisms 420 and 440.

Figure 5:
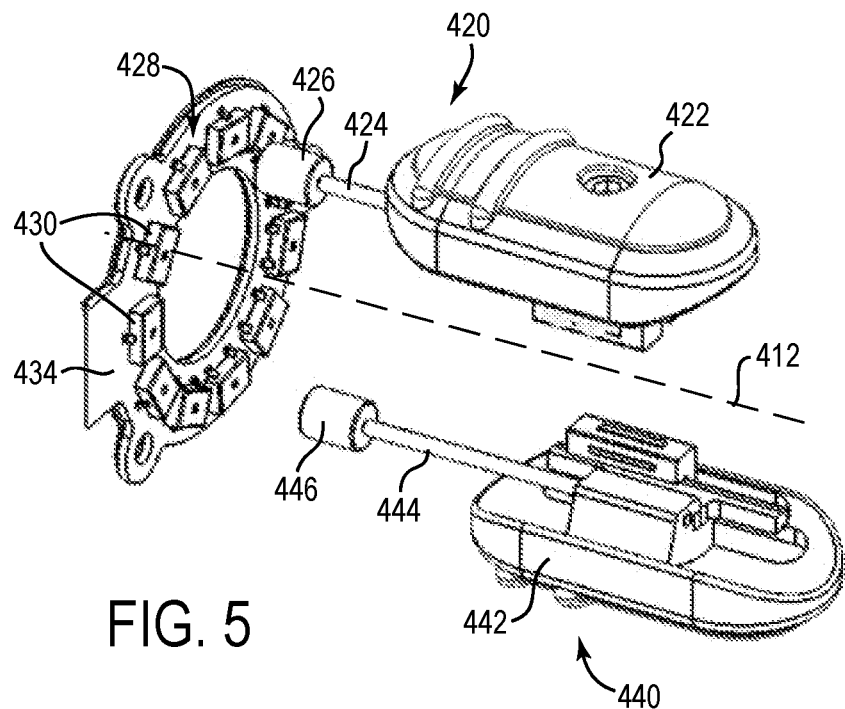
FIG. 5 is a perspective view of the switch mechanisms and sensor array as described with reference to FIG. 4, according to some implementations.

FIG. 5 is a perspective view of the switch mechanisms 420 and 440 and the sensor array 428 as described with reference to FIG. 4, while omitting other components of the controller portion 400. First switch mechanism 420 includes first switch contact portion 422, first plunger 424, and first sensor element 426. Second switch mechanism 440 includes second switch contact portion 442, second plunger 444, and second sensing element 446. Sensor array 428 includes sensor array elements 430 arranged about the longitudinal axis 412 of the controller portion 400 on the substrate 434 (e.g., printed circuit board). Switch contact portion 422 is positioned in a first position in its switch degree of freedom in which the sensor element 426 is positioned at a first position, and switch contact portion 442 is positioned in a second position in its switch degree of freedom in which the sensing element 446 is positioned at a second position. The first position is closer to the sensing array 428 than the second position in this example. In some implementations, one or more of the sensing array elements 430 can distinguish these positions based on the strength of sensed magnet fields from sensor elements 426 and 446.

Figure 6:
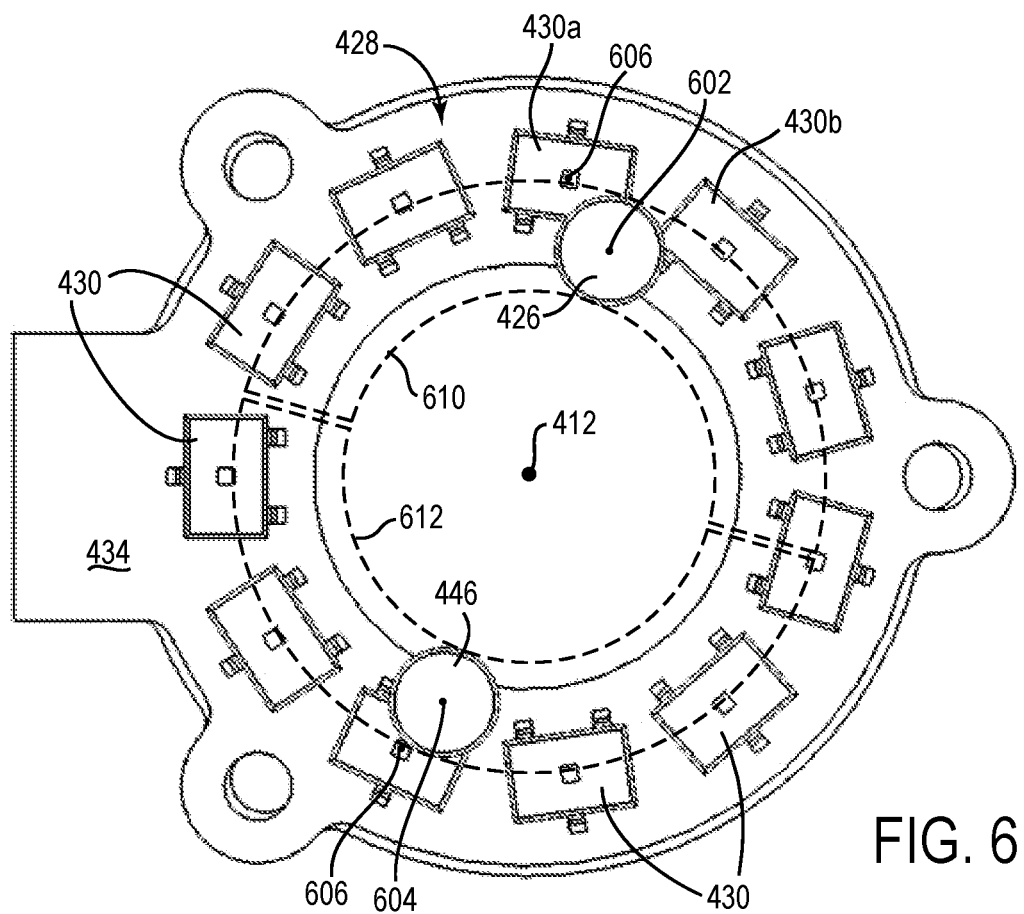
FIG. 6 is a side view of the sensor array and a portion of the switch mechanisms shown in FIG. 5, according to some implementations.

FIG. 6 is a side view of the sensor array 428 and a portion of the switch mechanisms 420 and 440. In this view, which shows a perspective parallel to axis 412, sensing elements (e.g., magnets) 426 and 446 of the switch mechanisms 420 and 440 are shown. Elements 426 and 446 rotate in conjunction about the axis 412 as the handle 402 rotates about axis 412. Sensor array elements 430 remain stationary with respect to the rotation of the elements 426 and 446.

Each sensor array element 430 can most strongly sense the magnetic field of the element 426 or 446 when the element 426 or 446 overlaps the greatest amount of area of that sensor array element 430 in the dimension of the central axis 412. In the example of FIG. 6, this situation occurs when the center of the first element 426 is radially aligned with the center of the sensory array element 430 in the perspective of FIG. 6, e.g., a line that is perpendicular to and intersects the axis 412 also intersects both such centers.

In the example view of FIG. 6, first sensor element 426 is shown partially overlapping two sensor array elements 430*a* and 430*b* in the dimension of the longitudinal axis 412. This causes both sensor array elements 430*a* and 430*b* to sense the first element 426, e.g., sense a magnetic field of a magnetic first element 426. In this example, sensor array element 430*a* is overlapped by first element 426 to a greater extent than sensor array element 430*b*, thus causing sensor array element 430*a* to sense a stronger magnetic field from the first element 426 than sensed by sensor array element 430*b*.

From the shown position, if first element 426 is rotated in a particular direction about axis 412, then the magnetic field of the first element 426 will be more strongly sensed by the sensor array element 430 that is in the direction of the rotation while the first element 426 overlaps more area of the sensor array element. The magnetic field will be more weakly sensed by the sensor array element in the direction opposite to the rotation, as the first element 426 moves away from and eventually no longer overlaps that sensor array element. For example, if first element 426 is rotated in a clockwise direction from the position shown in FIG. 6, the overlap of first element 426 with sensor array element 430*a* will be reduced and the overlap with sensor array element 430*b* will be increased.

In some implementations, sensor array 428 and sensor elements 426 and 446 are configured such that at least a portion of at least one sensor array element 430 is overlapping first element 426. Furthermore, when using two switch mechanisms as shown, at least a portion of at least one other sensing array element 430 is overlapping the second element 446.

In some implementations, the elements 426 and 446 have magnetic poles facing the sensor array 428 that are opposite in polarity to each other. For example, if first element 426 has a north pole facing the sensor array 428, then second element 446 has a south pole facing the sensor array 428, or vice-versa. The magnetic field from each type of magnetic pole produces a different output signal from the sensor array elements 430. This allows the sensor array 420 to distinguish sensing of the first switch mechanism 420 and the second switch mechanism 440.

In the example of FIG. 6, the sensor elements 426 and 446 do not fully overlap the sensor array elements 430. For example, the center 602 of element 426 and center 604 of element 446 are not at the same distance (e.g., radius) from the axis 412 as the centers 606 of the sensor array elements 430. This configuration may be implemented based on physical constraints in the controller portion 400, e.g., dimensions of packaging or housing in which the switch mechanism is housed may prevent the centers 602, 604, and 606 from being at the same radius. In some implementations, the centers of elements 426 and 446 can be provided at the same radius as the centers of sensor array elements 430, e.g., to enable sensing of the elements 426 and 446 over a larger area of the sensor array elements 430.

In some implementations, the sensor array elements 430 can have different sizes, sensing areas, and/or radial lengths than described above. For example, each sensor array element 430 can cover a greater or lesser angular range about the central axis 412, e.g., to allow a greater number or a fewer number of sensor array elements 430 spaced regularly about the central axis. In some implementations, one or more of the sensor array elements 430 can have different radial lengths than other sensor array elements 430.

In some implementations, additional switch mechanisms can be provided. For example, a third switch mechanism can be implemented similarly to switch mechanisms 420 and 440. In some examples, a third sensing element can be provided similarly to sensing elements 426 and 446, where, for example, the three sensing elements are angularly spaced approximately equidistant from each other around the axis 412. Similarly, a fourth switch mechanism can be provided, such that four sensing elements are spaced around axis 412, e.g. at 90-degree intervals.

In some implementations, a longer or smaller sensor element 426 and/or 446 can be used. For example, a sensor element 426 and/or 446 that extends over a larger angular range can be used. In some examples, a portion of a ring magnet is used in place of the respective smaller elements 426 and 446, e.g., the elements 426 and 446 can each be a portion of a ring magnet. In some examples, a sensor element 426 that extends over about 180 degrees and a sensor element 446 that extends over about 180 degrees can be used, such that each plunger 424 and 444 is coupled to an approximately half-circle shaped magnet.

For example, as shown in FIG. 6, in place of element 426, a half-ring magnet 610 (shown in dashed lines) can be coupled to the end of plunger 424, and in place of element 446, a half-ring magnet 612 (shown in dashed lines) can be coupled to the end of plunger 444. Due to the larger areas of the half-ring magnets 610 and 612, where each half-ring magnet covers a larger angular range than the elements 426 and 446 (in the view of FIG. 6), fewer sensor array elements 430 can be employed in sensor array 428. For example, e.g., three or four of the shown array elements 430 can be spaced regularly about axis 412, allowing a respective sensor array element 430 to always be overlapped at least partially by each half-ring magnet 610 and 612. This allows the sensor array 428 to sense the magnets 610 and 612 at any angular position of the switch mechanisms about axis 412.

Figure 7:
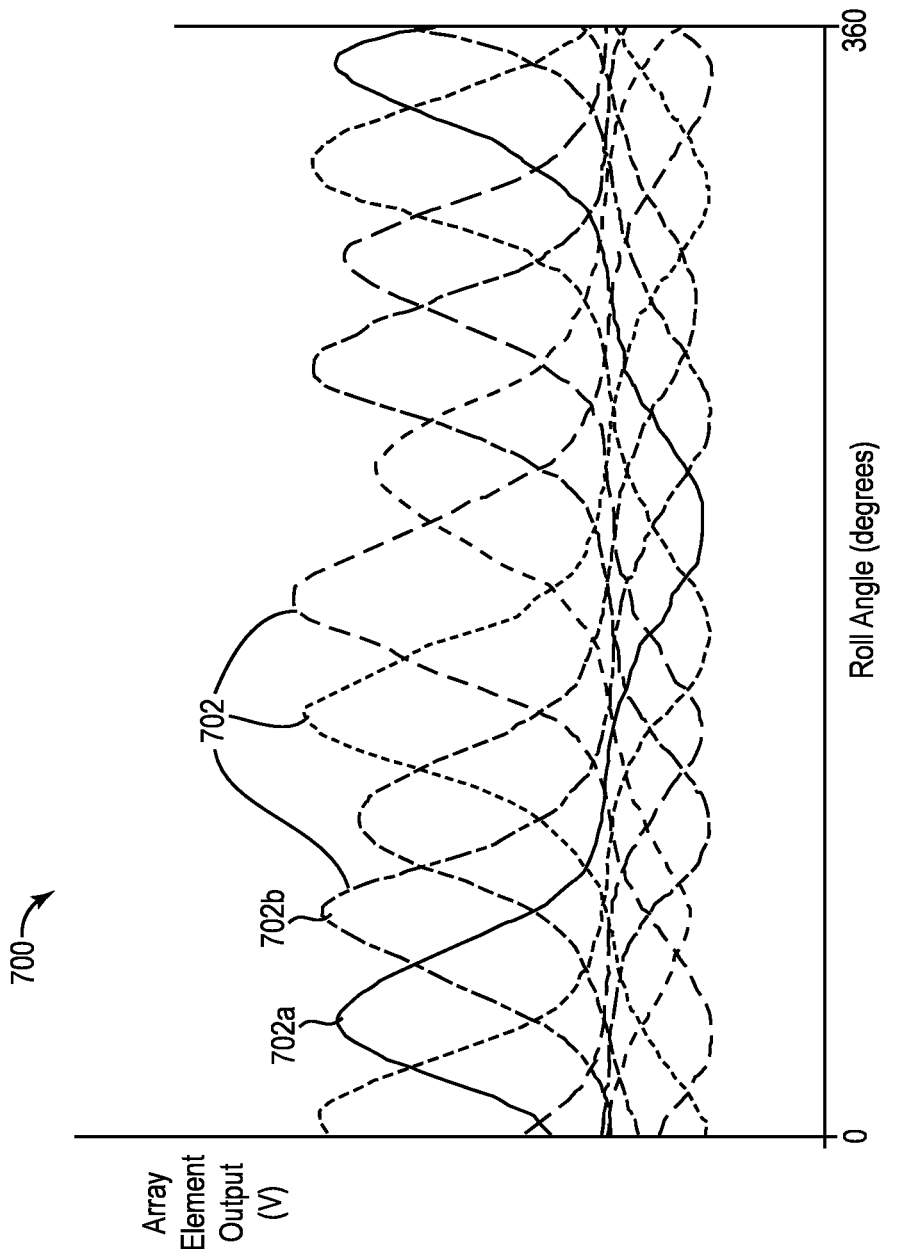
FIG. 7 is a diagrammatic illustration of a graph showing example waveforms illustrating raw signals output by an example sensor array during rotation of a handle, according to some implementations.

FIG. 7 is a diagrammatic illustration of a graph 700 showing example waveforms illustrating raw signals output by an example sensor array 428 of the controller portion 400 of FIG. 4 during rotation of a handle 402. In this example, sensor array elements 430 can be Hall effect sensors that output signals based on positions of sensor elements such as element 426 and element 446 with respect to the sensor array elements 430. Other implementations can use different types of sensors and waveforms. Graph 700 has a vertical dimension indicating a voltage scale, e.g., the voltage of an output signals of the sensor array. Graph 700 has a horizontal dimension indicating a roll angle about the axis 412.

A number of waveforms 702 are illustrated in graph 700 which indicate the individual raw output signals of individual sensor array elements 430 of the sensor array 428. For example, waveform 702a can be based on output from a first sensor array element 430, waveform 702b can be based on output from a second sensor array element 430 adjacent to the first sensor array element, etc. The waveforms 702 can be generated during a rotation of the handle 402 over the full rotational range of the handle 402. For example, the handle 402 is rotated 360 degrees about axis 412 in one direction such that the sensor elements 426 and 446 are rotated 360 degrees, while the switch mechanisms 420 and 440 are at a single position in the switch degree of freedom (e.g., the sensor elements 426 and 446 are at a constant distance from the sensor array 428). In this example, the switch mechanisms 420 is at a middle position (e.g., a nominal position) in its switch degree of freedom, and switch mechanism 440 is at a back position (e.g., a pull position) that is further from the sensor array 428 than the position of switch mechanism 420.

Waveforms 702 have amplitudes (e.g., indicating voltages) based on a position of the sensor elements 426 and/or 446 with respect to the sensor array 428. For example, the amplitudes of the waveforms 702 can be based on a distance of the elements 426 and/or 446 to the sensor array 428 along a linear axis that is parallel to the central axis 412 of FIG. 4.

In the example described, a positive voltage is output by a sensor array element 430 (e.g., Hall effect sensor) when sensing a particular first polarity of a magnetic field, and a negative voltage is output by that sensor array element 430 when sensing a second polarity of a magnetic field that is opposite to the first polarity. In this example, sensing a north pole of a magnet causes a positive voltage output by the sensor array element 430, and sensing a south pole causes a negative voltage output. Other sensors can output different voltages in response to sensing particular magnetic field polarities.

Each waveform 702 has a maximum voltage and a minimum voltage. The maximum voltage of a waveform occurs when a magnet pole facing the sensor array is a first pole and the magnet has a maximum amount of overlap with the sensor array element outputting that waveform. In one example, a north pole of sensor element 426 is facing the sensor array 428, and the maximum voltage is output by a sensor array element when element 426 has maximum overlap with that sensor array element.

The minimum voltage of a waveform occurs when a magnet pole facing the sensor array is a second pole, having opposite polarity to the first pole, and the magnet has a maximum amount of overlap with the sensor array element outputting that waveform. In one example, a south pole of element 446 is facing the sensor array, and the minimum voltage is output by a sensor array element 430 when element 446 has maximum overlap with that sensor array element. In this example, the minimum voltage is the (negative) peak of the voltage sensed by a sensor array element 430 for the second polarity.

In some implementations, the waveforms 702 of FIG. 7 may have varying maximum amplitudes and minimum amplitudes, as shown, e.g., due to variations in sensing conditions and in the sensor array elements.

Figure 8:
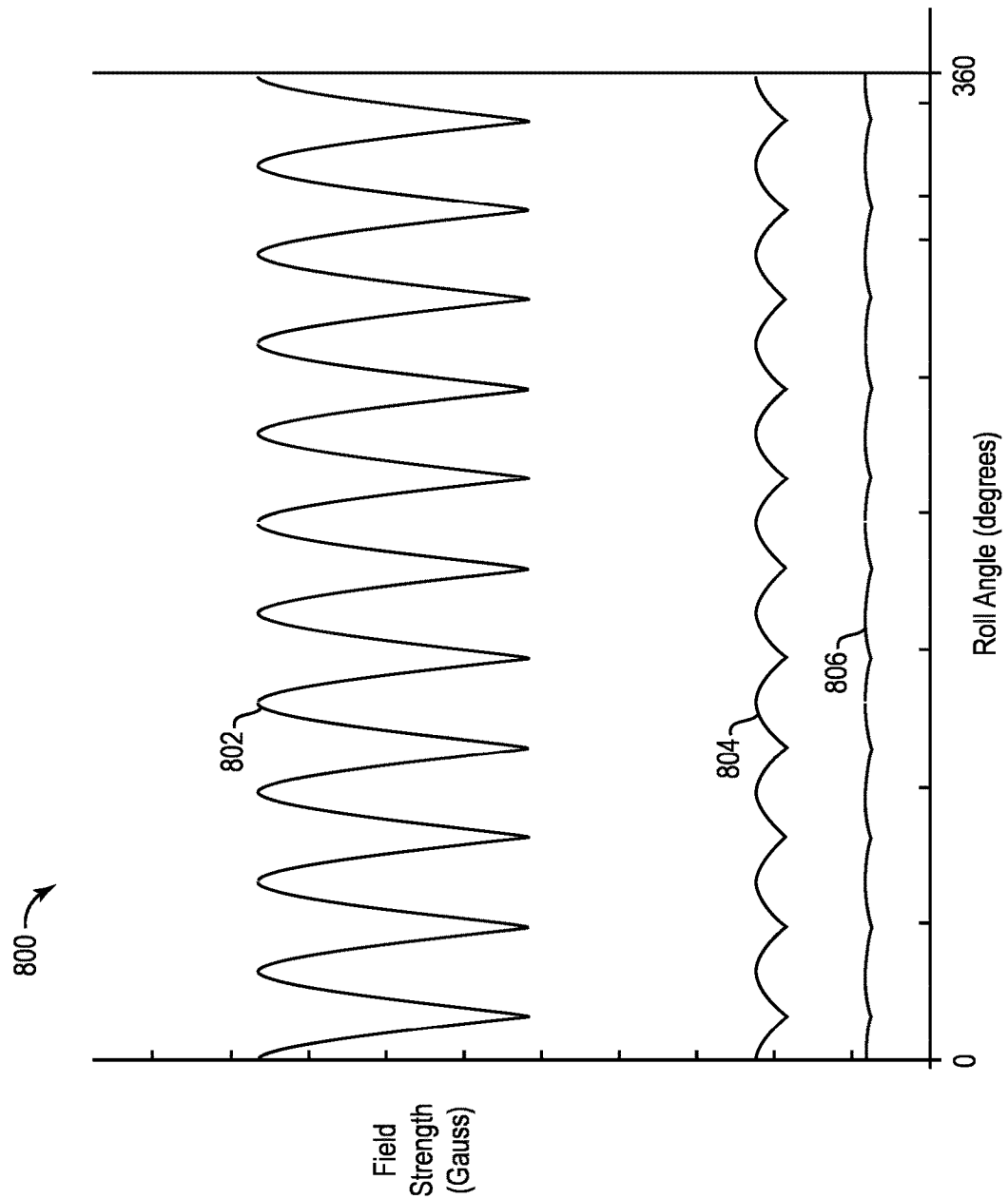
FIG. 8 is a diagrammatic illustration of a graph showing example waveforms resulting from processing output signals provided by the example sensor array at different switch positions, according to some implementations.

FIG. 8 is a diagrammatic illustration of a graph 800 showing example waveforms resulting from processing output signals provided by the example sensor array 428 at different switch positions. Graph 800 has a vertical dimension indicating a field strength scale (e.g., in Gauss units), which corresponds to a voltage output magnitude. In this example, a horizontal dimension indicates a rotational angle range of the switch mechanism about axis 412, where the handle 402 has been rotated 360 degrees.

Graph 800 shows the result of applying a maximum filter on the outputs of the sensor array elements 430 that have sensed the sensor element 426 as the switch mechanism 420 (and element 426) are rotated about axis 412. For example, the maximum filter is applied to waveforms similar to those shown in FIG. 7 (the waveforms can have a more constant magnitude to obtain the waveform 802, compared to the waveforms of FIG. 7). The result is the maximum values that were output by the sensor array 428 by all the sensor array elements 430.

Waveform 802 shows the maximum filter applied to the waveforms output by the sensor array elements 430 while the switch mechanism 420 is rotated and is positioned at a close distance to the sensor array 428 (e.g., at the push position) in the switch degree of freedom. Waveform 802 is made up of the highest amplitudes of the various signals output by from the sensor array elements 430.

Waveform 804 shows the maximum filter applied to the waveforms output by the sensor array elements 430 while the switch mechanism 420 is rotated and is positioned at a mid-range distance to the sensor array 428 (e.g., at a middle position) in the switch degree of freedom, where the mid-range distance is greater than the close distance associated with waveform 802. Waveform 804 is made up of the highest amplitudes of the various signals output by the sensor array elements 430. Waveform 804 is lower in amplitude than waveform 802 since the element 426 is further from the sensor array 428, causing the sensed magnetic field to be weaker.

Waveform 806 shows the maximum filter applied to the waveforms output by the sensor array elements 430 while the switch mechanism 420 is rotated and is positioned at a further distance to the sensor array 428 (e.g., at a pull position) in the switch degree of freedom, where the further distance is greater than the mid-range distance associated with waveform 804. Waveform 806 is made up of the highest amplitudes of the various signals output by the sensor array elements 430. Waveform 806 is lower in amplitude than waveforms 802 and 804 since the element 426 is further from the sensor array 428, causing the sensed magnetic field to be weaker.

Figure 9:
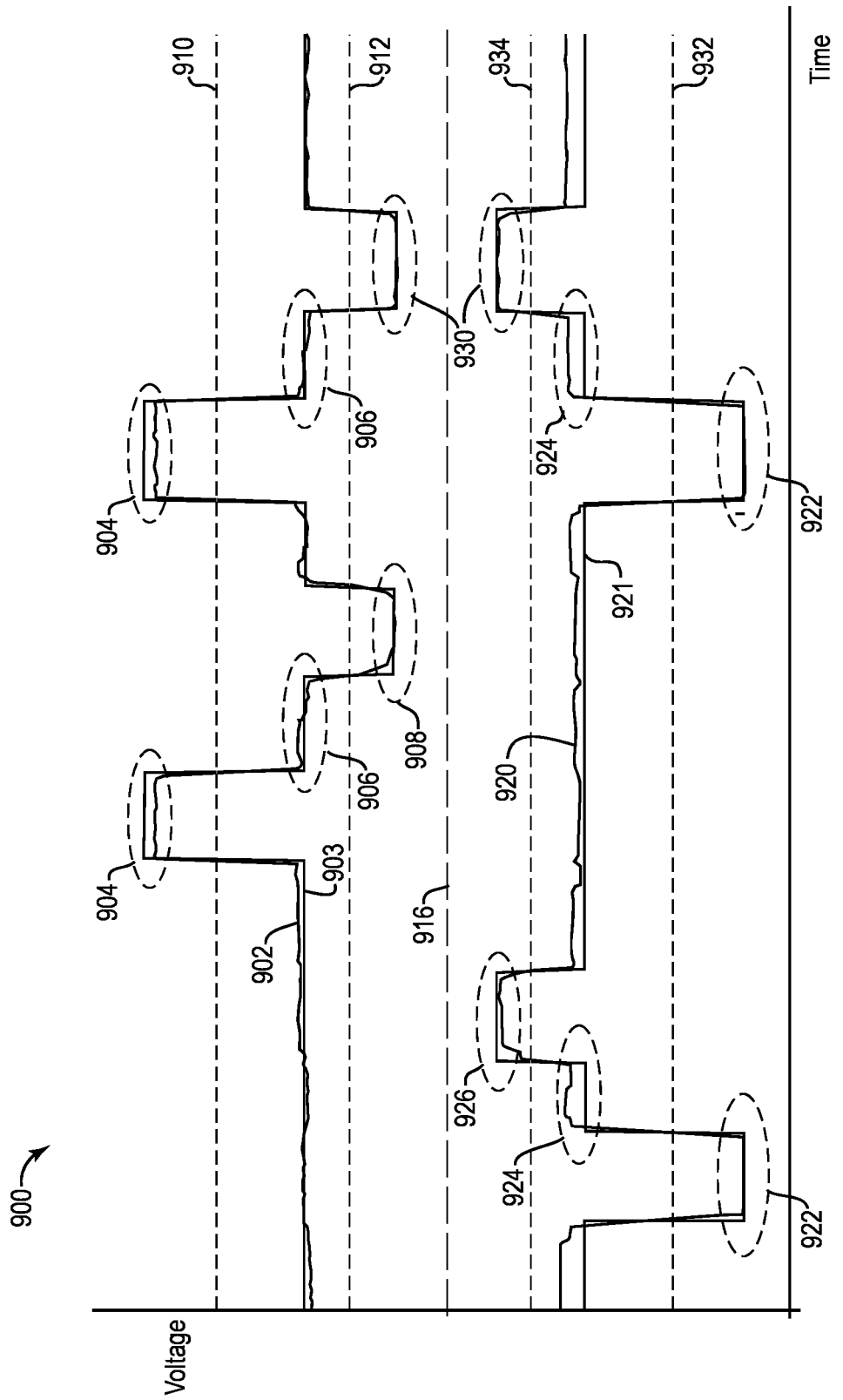
FIG. 9 is a diagrammatic illustration of a graph showing example waveforms based on output signals provided by the example sensor array, according to some implementations.

FIG. 9 is a diagrammatic illustration of a graph 900 showing example waveforms based on output signals provided by the example sensor array 428. Graph 900 has a vertical dimension indicating a voltage scale and a horizontal dimension indicating a time range. In this example, the handle 402 is not rotated, causing the signals output from the sensor array elements 430 to be approximately constant, e.g., in contrast to the signals of FIGS. 7 and 8.

In the example of FIG. 9, a first waveform 902 is associated with the first switch mechanism 420 (including sensor element 426). In this example, first waveform 902 is an analog waveform representing analog voltages sensed by the sensor array elements 430. The first waveform 902 has an amplitude based on the individual outputs from the sensor array elements 430. For example, the first waveform 902 can be formed by applying a maximum filter among all of the outputs of the individual sensor array elements 430 to obtain the highest voltage output by any of the sensor array elements 430, and using the highest output value as the current value for waveform 902.

In this example, a first processed waveform 903 is determined from the first waveform 902. First processed waveform 903 can be a digital waveform set at or latched to particular states or levels (amplitudes) based on the amplitude of the first waveform 902 relative to thresholds, as described below.

Different amplitudes of the first waveform 902 can indicate different particular positions of the first switch mechanism 420 in its linear degree of freedom. First waveform 902 decreases in amplitude as sensor element 426 is moved further from the sensor array 428. In this example, first waveform 902 has a high amplitude 904 at particular times, which is the maximum amplitude sensed for the output signal of the sensor array 428 in this example. Amplitude 904 is sensed (and corresponds to) when the first switch contact portion 422 and the element 426 are at the forward position closest to the sensor array 428 within their linear range of motion.

First waveform 902 changes to a middle amplitude 906 from the high amplitude 904, e.g., in response to the first switch mechanism 420 being moved by the hand of a user to the middle position in the switch degree of freedom, thus causing element 426 to be at a middle position in its linear movement range. This motion moves the element 426 further from the sensor array 808, causing the reduction in sensed amplitude. In various implementations, the amplitude of the first waveform 902 may change linearly or non-linearly in correspondence with the change of position of the element 426 in the linear degree of freedom of the switch mechanism 420. First waveform 902 moves from the middle amplitude 906 to a low amplitude 908, which in this example is in response to the first switch mechanism 420 being moved to a further (e.g., furthest) position from the sensor array 428, e.g., the back position.

By sensing the amplitude of waveform 902 and comparing the amplitude to one or more threshold values, the position the first switch mechanism 420 is determined. For example, the high amplitude 904 is above a first threshold 910, indicating that the switch mechanism is in the forward position. The middle amplitude 906 is detected below the first threshold 910 and above a second threshold 912, indicating that the switch mechanism is in the middle position. The low amplitude 908 is detected below the second threshold 912, indicating that the switch mechanism is in the back position. The waveform 902 has been filtered to be the maximum value provided by the sensor array elements 430 before it is compared to the thresholds, such that the low amplitude 908 is higher than the maximum value of the waveform 920 for the second switch, described below.

In this example, first processed (digital) waveform 903 is changed from a middle state that is close to middle amplitude 906 to a high state close to high amplitude 904 when the first waveform 902 goes above the threshold 910. Similarly, first processed waveform 903 is changed from the high state to the middle state when the first waveform 902 goes below the threshold 910. First processed waveform 903 is changed from the middle state to a low state close to low amplitude 908 when the first waveform 902 goes below the threshold 912. First processed waveform 903 is changed from the low state to the middle state when the first waveform 902 goes above the threshold 912.

In this example, a second waveform 920 is associated with the second switch mechanism 440. Second waveform 920 determined based on output from the sensor array 428 that is based on the position of second magnet 446. In this example, second waveform 920 is shown with respect to the same timescale (horizontal axis) used for first waveform 902. In this example implementation using magnets, the sensor array elements 430 output a different range of voltage signals when detecting second magnet 446 (e.g., the second magnet 446 provides different polarity of magnetic field than first magnet 426), and the voltage signals move in the opposite direction to the first magnet 426. Thus, in first waveform 902, higher magnitudes move in a positive direction of the voltage axis above a center voltage 916, and in second waveform 920, higher magnitudes move in a negative direction of the voltage axis below the center voltage 916.

In this example, second waveform 920 is an analog waveform representing analog voltages sensed by the sensor array elements 430. Second waveform 920 has an amplitude (e.g., voltage) based on the individual outputs from the sensor array elements 430. For example, the second waveform 920 can be formed by applying a minimum filter among all of the outputs of the individual sensor array elements 430 to obtain the lowest voltage output by any of the sensor array elements 430. The lowest output value is used as the current value for second waveform 920.

In this example, a second processed waveform 921 is determined from the second waveform 920. Second processed waveform 921 can be a digital waveform set at particular states or levels (amplitudes) based on the amplitude of the second waveform 920 relative to thresholds, as described below.

Second waveform 920 decreases in amplitude as the second sensor element 446 is moved closer to the sensor array 428. In this example, this is due to the second element 446 including a magnet having a pole facing the sensor array, where the pole is opposite polarity to the pole of the magnet of first element 426 that is facing the sensor array. For example, the second waveform 920 can be based on a south pole of the element 446 facing the sensor array 428, while first waveform 902 can be based on a north pole of the element 426 facing the sensor array 428. In some implementations, these facings can be reversed, such that the magnet 426 is associated with a waveform that goes negative in amplitude when positioned further from the sensor array 428.

Low amplitude 922 of second waveform 920 is the lowest amplitude sensed in this example. Low amplitude 922 is sensed (and corresponds to) when the second switch mechanism 440 is at a position closest to the sensor array 428 within the switch degree of freedom (thus corresponding to the highest strength magnetic field sensed from second magnet 446). The second waveform 920 is at a middle amplitude 924, e.g., in response to the second switch mechanism 440 being at or moved by the user to a middle position in the linear degree of freedom of the second switch mechanism 440. In this example, when the second waveform 920 is at high amplitude 926, the second switch mechanism 440 is at a position further (e.g., furthest) from the sensor array 428 within the switch degree of freedom. In various implementations, the amplitude of the second waveform 920 may change linearly or non-linearly in correspondence with the change of position of the element 446 in the linear degree of freedom.

By sensing the amplitude of waveform 920 and comparing the amplitude to one or more threshold values, the position the second switch mechanism 440 is determined. For example, low amplitude 922 is below a third threshold 932, indicating that the switch mechanism is in the forward position. Middle amplitude 924 is above the third threshold 932 and below a fourth threshold 934, indicating that the second switch mechanism is in the middle position. High amplitude 926 is detected above the fourth threshold 934, indicating that the second switch mechanism is in the back position.

In this example, the second processed (digital) waveform 921 is changed from a middle state that is close to middle amplitude 924 to a low state close to low amplitude 922 when the second waveform 920 goes below the third threshold 932. Similarly, second processed waveform 921 is changed from the low state to the middle state when the second waveform 920 goes above the threshold 932. Second processed waveform 921 is changed from the middle state to a high state close to high amplitude 926 when the second waveform 920 goes above the fourth threshold 934. Second processed waveform 921 is changed from the high state to the middle state when the second waveform 920 goes below the threshold 934.

The different pole facings of the sensor element 426 and sensor element 446 allow both sensor elements to be sensed independently and simultaneously based on obtaining maximum and minimum values from the sensed voltages. This allows the switch positions of the switch mechanisms 420 and 440 to be detected simultaneously. For example, simultaneous activations or user manipulations of the first switch mechanism 420 and second switch mechanism 440 can be sensed simultaneously. In some examples, a simultaneous "pull" of the respective first and second switch mechanisms 420 and 440, e.g., movement in the same directions in their degrees of freedom, can be detected, e.g., as shown in graph 900 by the waveform portions 930 changing amplitude at the same time. Similarly, a simultaneous "pull" and "push" of the first and second switch mechanisms can be detected in different directions in their degrees of freedom to different switch positions.

Additional, fewer, and/or different thresholds can be used in other implementations to detect multiple positions of a switch mechanism.

In some implementations, other types of sensors can be used in sensor array 428 in place of or in addition to magnetic elements and sensors as described above. In some examples, other types of multiple individual sensors can be arranged in an array, e.g., around an axis of rotation, similarly to sensor array elements 430 of sensor array 428. For example, one or more individual inductive sensors can be used (e.g., as array elements 430) in sensor array 428, and the sensor elements 426 and 446 can include pieces of metal instead of magnets. The metal can be a type of metal that can be sensed by the array elements in the range of motion of the switch mechanism, such as a ferrous metal, steel, etc. In some implementations, similar physical arrangements of the individual sensors can be used as described herein for other types of sensors. Other types of non-contact proximity sensors can be used for the sensor array 428.

In some implementations, one or more capacitive sensors can be used, e.g., as array elements 430, in the sensor array 428 to sense the proximity of a sensor element 426 (e.g., a piece of conductive material) that can be moved with the switch contact portion 422. In some examples, one or more coils can be used as a capacitive sensor for sensor array 428, e.g., a single coil in place of sensor array 428, or multiple coils spaced around axis 412 in sensor array 428. In some implementations, one or more such base member coils can also be used to transfer power across the rotary joint. For example, one or more corresponding second coil(s) can be fixed to the handle 402 facing the base member coil(s) on the base member, such that power is transferred from the base member coil(s) to the handle coil(s). In some of these implementations, the handle coil(s) can sense the proximity of the sensor element 426 and/or 446 instead of or in addition to the base member coil(s) sensing the sensor element, and the handle coil(s) can thus detect the position of the switch in its switch degree of freedom. For example, data indicating such a detected switch position can be sent to the base member, e.g., using an optical sensor (emitter and detector across the rotary joint) or other type of sensor.

In some implementations, one or more optical sensors can be used. For example, one or more optical detectors can be included in the base sensor element such as sensor array 428. In some examples, the optical detectors can be array elements arranged in the sensor array 428 to sense the proximity of an object that can be moved with the switch mechanisms. In some examples, photoelectric sensors can be used, where, e.g., an emitter light source (Light Emitting Diode (LED), laser diode, etc.) transmits a beam of electromagnetic energy (e.g., visible light, infrared light, etc.), and a detector (e.g., a photodiode or phototransistor receiver, charge coupled device (CCD), etc.) detects the emitted electromagnetic energy. For example, the emitter can transmit a beam of visible or infrared light to the detector. In some examples, element 426 (can block one or more beams of light emitted by one or more array elements 430 at particular distances from the sensor array, thus allowing detection of a distance of the element 426 from the sensor array 428. In some implementations, such a blocking element 426 can reflect back light at different magnitudes to a detector in sensor array 428, which can determine the distance of the element 426 based on the detected light.

For example, in some implementations, optical time-of-flight sensors can be used, which can measure the time taken by an emitted beam of light to reflect from a surface and return to a detector, e.g., a detector located adjacent to or otherwise near to the emitter, and thus deduce the distance of an object from the emitter. In another example using an optical sensor, the magnitude of a reflected beam can be detected to determine a distance of a surface which reflected the beam. In some implementations, an ultrasonic sensor can similarly transmit sonic pulses and sense the time to detect pulses reflected from the sensor element 426, and/or detect magnitudes of reflected pulses to indicate distance of the sensor element from the sensor or sensor array.

In some implementations using proximity sensors such as time-of-flight sensors, the density of sensor array elements (e.g., elements 430) may be reduced, since the sensor provides an actual measure of axial distance. In contrast, Hall effect sensors provide detected field strengths from which an axial distance is inferred. For example, three time-of-flight sensors may be included as elements 430 which can be positioned, for example, about axis 412 at 120 degrees apart. Two optical paddles can be provided as sensor elements 426 and 446, which are each provided as a semi-circular ring that covers 180 degrees of the rotation (e.g., similar to half-ring magnets 612), thus allowing full sensing coverage of handle rotation.

In another example implementation using an optical sensor, an emitter of sensor array 428 can send a beam of light (e.g., laser) to a splitter, which directs the beam to a surface that is included in or connected to the switch mechanism 420 or 440. The surface reflects the beam to a detector connected to the base member (e.g., housing 409). The surface includes areas or regions having different colors at different positions along the surface such that a different color receives the directed beam at different switch positions in the switch degree of freedom. The color of the surface is indicated in the beam of light reflected from the surface, and the switch position is determined based on the particular reflected color detected. In some implementations, various types of fiducial patterns can be provided on a sensor element 426 or 446, which can be sensed by one or more sensors of sensor array 428. For example, patterns of lines, dots, one-dimensional or multi-dimensional barcodes, and/or other markings can be provided and sensed by a camera or other type of sensor, where the size of detected markings can indicate a distance between the detector and element.

In some implementations, a touch sensor can be provided in addition to or in place of the switch mechanism 420 and/or 440. For example, the touch sensor can include a touch surface that is provided on the handle 402 on the top surface of the switch contact portion 422 and/or 442, or in place of these switch contact portions. The touch sensor can be configured to sense a location of user touch on the touch surface. In some examples, the touch surface can cover a surface area of the handle 402 similar to the surface area covered by switch contact portion 422 as described herein, or can cover a larger or smaller surface area.

In some implementations, the surface area of the touch surface can be divided into different command zones or areas, each zone corresponding to a different command and causing the associated command to be issued to the control system when that zone is detected as being touched by the user. For example, a location of the user touch on the touch surface can be sensed as a position of the switch, e.g., a forward, middle, back position as described herein, corresponding to forward, middle, and back zones defined on the surface area of the touch sensor. Any of other positions in one or two dimensions of the touch surface (e.g., left, right, forward left, back right, etc.) can also or alternatively be sensed by the touch sensor, with corresponding zones defined on the touch surface. In some implementations, the different command zones of the touch surface can be indicated haptically to the user via physical features, e.g., ridges, bumps, or other features provided on the touch surface.

In some implementations, a touch of a user on the touch surface will cause a change to, or activation of, the corresponding switch position (e.g., by the control system) only if the user's touch is continuously sensed on the touch surface (e.g., in a single zone) for an amount of time over a time threshold. In some implementations, different command zones of the touch sensor can be associated with different time thresholds for such activation.

In some examples, the touch sensor can include a capacitive sensor surface, e.g., a similar sensing system as used in touchscreens currently available on cell phones and similar devices. In various implementations, the touch surface can also include display capability (displaying pixels as for a touchscreen), e.g., can display various indicators of switch state as colors, icons, etc., or display other information related to the control system, slave device, etc. In some implementations, a resistive sensor surface can be used, similar to a resistive touchscreen.

In some implementations, power and communication channels can be provided to the touch sensor across the rotary joint between the handle 402 and the base member to allow continuous rotation of the handle with respect to the base member as in other implementations described herein. For example, a rotary transformer can be used to transmit power across the rotary joint, in which a first coil is fixed to the base member and a second coil is fixed to the handle 402 and power is transferred between the coils. Data from or to the touch sensor can be communicated via optical sensor or other type of sensor across the rotary joint, e.g., an optical data transmitter on the handle can transmit data by emitting electromagnet energy through an axial passage extending between the first and second coils, and an optical data receiver/detector on the base member can detect the emitted energy. In some examples, coils can be similarly used as described with reference to U.S. Pat. No. 8,073,335 B2 (filed Sep. 30, 2008), which is incorporated herein by reference in its entirety. In some implementations, a slip ring or other mechanism can be used to transfer power to and data to/from the touch sensor across the rotary joint.

In some implementations using the touch sensor, the rotational position of the handle 402 can be detected similarly as described above. For example, a plunger and sensor element similar to plunger 424 and sensor element 426 can be coupled to the touch sensor or to a side of the touch surface, where the sensor element 426 rotates about axis 412 with the handle 402 similarly as described herein (and, e.g., does not translate linearly parallel to axis 412). The rotational position of the sensor element 426 about axis 412 can be detected by a sensor array 428 on the base member, similarly as described herein.

Figure 10:
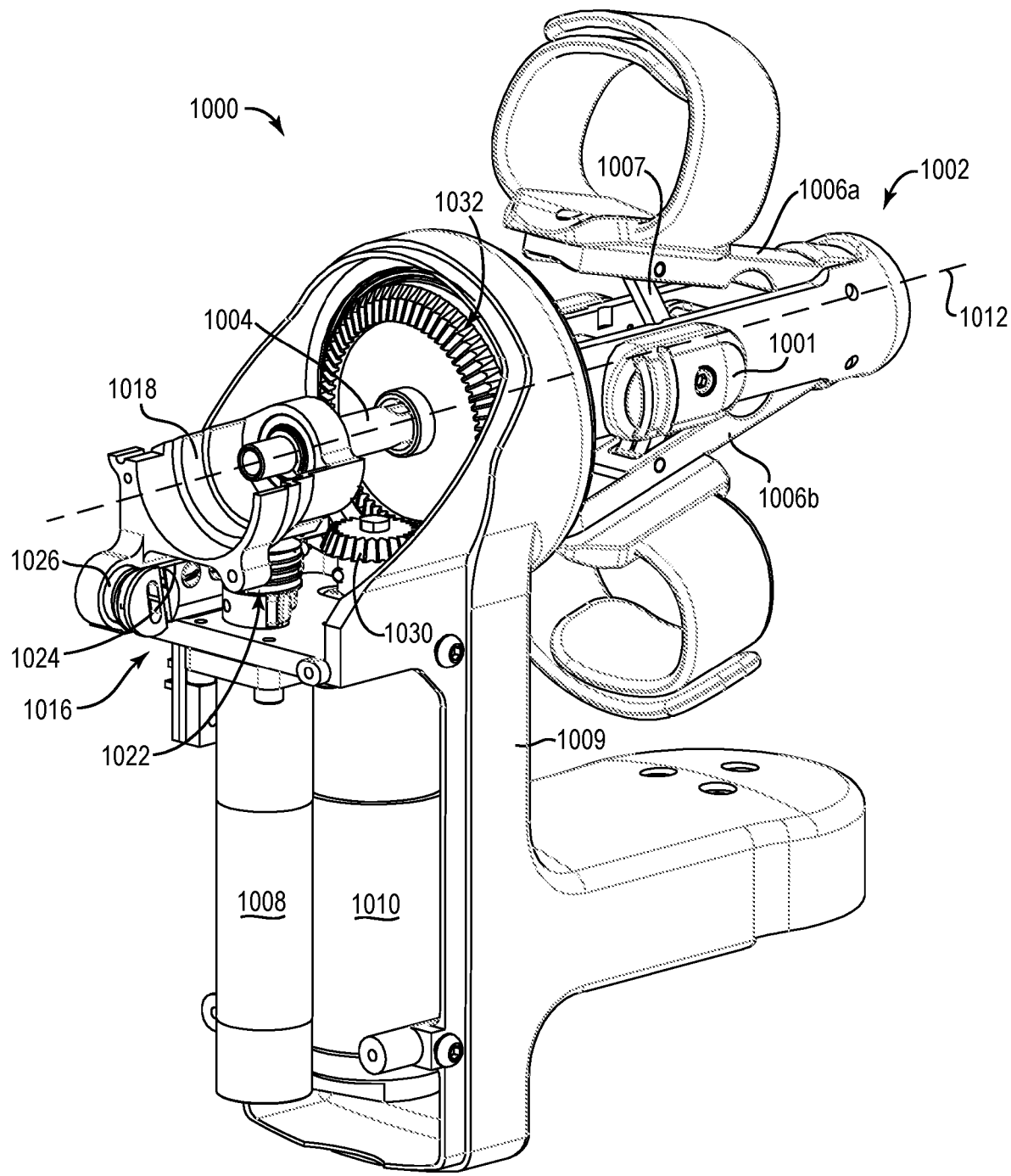
FIG. 10 is a perspective view of an example implementation of a portion of a control input device that can provide forces in the degrees of freedom of grips of a handle, according to some implementations.

FIG. 10 is a perspective view of an example implementation of a controller portion 1000 that can provide forces in the degrees of freedom of grips of a handle of a control input device, which can be used in some implementations with switch mechanisms described herein. Other configurations of actuators and force transmission mechanisms can be used in other implementations.

In some implementations, a handle 1002 can be similar to the handle 402 of controller portion 400 as described above with respect to FIG. 4, or a different handle or control input device can be used. One or more contact switches 1001 can be provided on the handle 1002 and operate similarly as described in various implementations herein.

A main shaft 1004 can be connected to and drive grip members 1006a and 1006b, e.g., via a respective mechanical linkage 1007 rotatably coupled between each grip member 1006 and the main shaft 1004. For example, main shaft 1004 can be used for main shaft 404 of FIG. 4.

An actuator 1008 can be provided to drive linear motion of the main shaft 1004 along longitudinal axis 1012. In some implementations, actuator 1008 can be a rotary DC gear motor or other type of rotary actuator. In some examples, actuator 1008 can be rigidly mounted to the link (e.g., housing) 1009 and oriented such that its shaft rotates about an axis that is oriented perpendicular (90 degrees) to the axis 1012.

Main shaft 1004 can be connected to a capstan mechanism 1016 provided between the main shaft 1004 and an actuator 1010. The capstan mechanism 1016 includes a linear carriage 1018 that is coupled to the main shaft 1004. The main shaft 1004 can be rotated independently of the linear carriage 1018. The linear carriage 1018 can move linearly, e.g., slide, upon a linear rail that is rigidly coupled to the link 1009 and aligned parallel to the main shaft. The capstan mechanism 1016 can include a capstan drum 1022 which is rigidly coupled to the rotating shaft of actuator 1008. The capstan drum 1022 is coupled to the linear carriage 1018 by a cable 1024. A first end of cable 1024 can be attached to a first portion of the carriage 1018 that is closest to the handle 1002. The cable 1024 is wrapped a number of times around the capstan drum 1022, and the second end of the cable 1024 can be attached at a second portion 1026 of the linear carriage 1018, e.g., the end or a portion of the carriage 1018 that is further from the handle 1002 than the first portion of the carriage 1018.

The driven rotation of the shaft of the actuator 1010 directly drives the constrained linear motion of the linear carriage 1018 and the main shaft 1004 via the cable 1024, thus causing forces on the grip members 1006a and 1006b to bias them toward open and closed positions in accordance with the linear motion of the main shaft 1004. In some implementations, transmission mechanisms other than the capstan mechanism 1016 can be used. For example, a rack and pinion mechanism or a drive wheel can be used.

In some implementations, an actuator 1010 (e.g., motor) can be rigidly mounted to housing 1009 and used to drive rotation of the handle 1002 about axis 1012. In this example, actuator 1010 is oriented such that its rotating shaft rotates about an axis that is oriented perpendicular (90 degrees) to the axis 1012 of the main shaft 1004. In this example, the actuator shaft is rigidly coupled to a roll bevel pinion 1030 that includes a number of teeth that engage a number of grooves/teeth of a roll gear 1032 and cause roll gear 1032 to rotate in response to rotation of the actuator shaft. This causes rotational forces to the handle 1002 about axis 1012.

In other implementations, actuator 1010 and/or actuator 1008 can be oriented such that their rotating shafts rotate about an axis that is parallel to the axis 1012 and, for example, the rotating shafts are connected to the main shaft 1004 by a transmission.

Similarly as described in various implementations herein, one or more sensors can be coupled to the handle 1002 and/or other components of the controller portion 1000 and can detect the positions of the grip members 1006a and 1006b in their degrees of freedom. For example, in some implementations, a rotary encoder can be included in the housing of actuator 1008 to detect rotation of the shaft of that actuator and thus linear motion of the main shaft 1004. In some implementations, a linear sensor can be coupled to the link 1009 to sense linear motion of the main shaft 1004 or linear carriage 1018. Similarly, one or more sensors can be coupled to one or more components of the controller portion 1000 to detect the roll orientation of the handle 1002 about axis 1012. For example, a rotary encoder can be included in the housing of actuator 1010 to detect such roll orientation based on actuator shaft rotation. The sensors can send signals describing sensed positions, orientations, or motion to one or more control circuits of the teleoperated system. In some modes or implementations, the control circuits can provide control signals to the slave device 104. The sensors can be any of a variety of types of sensors, e.g., a magnetic sensor (e.g., magnetic incremental linear position sensor, Hall Effect sensor, etc.), optical sensor, encoder, resistance sensor, etc.

In various implementations, the handle 1002 can be provided with additional degrees of freedom. In some examples, the controller portion 1000 can allow movement of the handle 1002 within the workspace of the master control workstation 102 with a plurality of degrees of freedom, e.g., six degrees of freedom including three rotational degrees of freedom and three translational degrees of freedom. One or more additional degrees of freedom can be sensed and/or actuated similarly as described above for the degrees of freedom.

Figure 11:
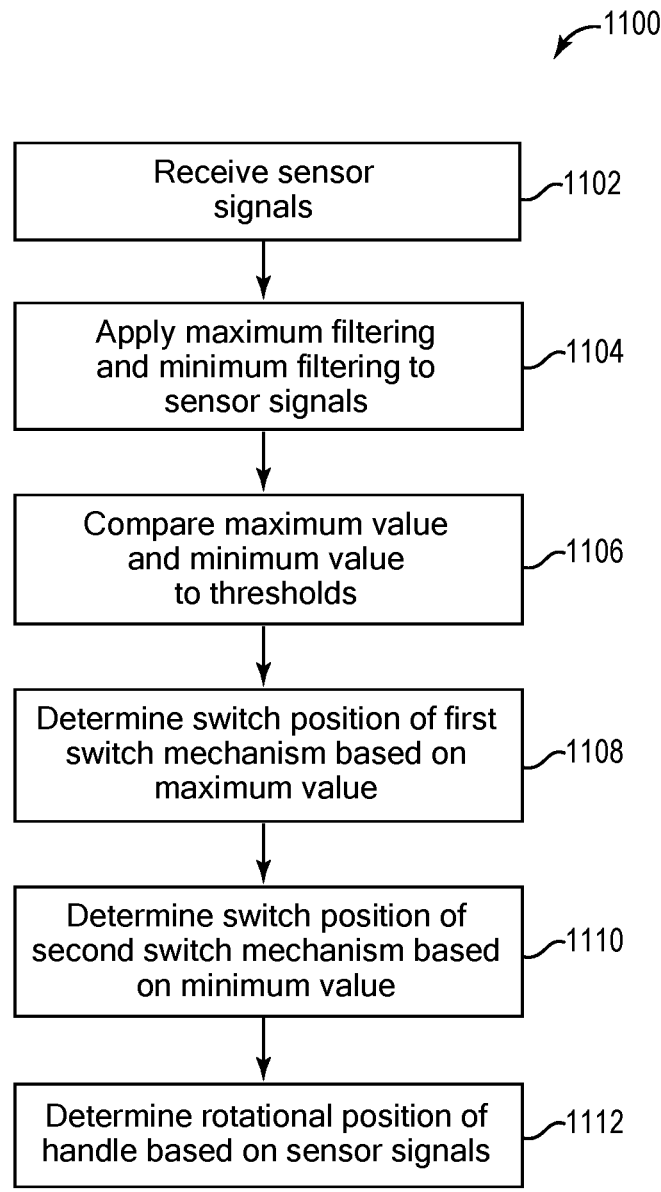
FIG. 11 is a flow diagram illustrating an example method to detect positions of control switches on a control input device, according to some implementations.

FIG. 11 is a flow diagram illustrating an example method 1100 to detect positions of control switches on a control input device. Method 1100 can, for example, be used with an example teleoperated system or other control system in which the control input device is a master control device (master controller) that controls a slave device. For example, in some implementations, the control input device is a component of a workstation, e.g., master control workstation 102 of FIG. 1, and method 1100 can be performed by a control circuit component of the master control workstation 102. In some examples, the control circuit can include one or more processors, e.g., microprocessors or other control circuits, some examples of which are described below with reference to FIG. 13. The master controller can be, for example, any of the master controller implementations described herein. Other implementations can use a control input device having one or more features described herein with other types of systems, e.g., non-teleoperated systems, a virtual environment (e.g., medical simulation) having no physical slave device and/or no physical subject interacting with a physical slave device, etc.

In block 1102, sensor signals are received. For example, sensor signals can be received as outputs from sensor array elements 430 of sensor array 428 as described herein. The sensor signals can describe the associated sensors' detection of sensed elements, such as sensor elements 426 and/or 446 coupled to a switch mechanism and moveable in respective switch degree of freedom, e.g., moveable to multiple switch positions. In some implementations, the sensor elements can also be rotated about a central axis, as described herein.

In block 1104, maximum filtering and/or minimum filtering can be applied to the received sensor signals to obtain switch position value(s) for each switch mechanism. In some examples, maximum filtering can be applied to sensor signals that have an amplitude that is greater in accordance with a closer position of a sensor element of a switch mechanism. For example, a sensor signal is output by a sensor array element 430 for a particular polarity of sensor element 426, where a larger amplitude is based on a higher strength of a detected magnetic field provided by that element, and where the magnetic field has a higher strength at a closer switch position to the sensor array.

In some implementations, minimum filtering can be applied to sensor signals that have an amplitude that is smaller (or having a negative magnitude) in accordance with a closer position of a sensor element of a switch mechanism. For example, a sensor signal is output by a sensor array element 430 for a particular polarity of sensor element 446, where a smaller amplitude is based on a higher strength of a detected magnetic field provided by that element, and where the magnetic field has a higher strength at a closer switch position to the sensor array.

In other implementations, other types of filtering and/or other signal processing can be used to obtain switch position values in block 1104. For example, a switch position value can be a sum of all the outputs of the sensor array elements 430 (e.g., a total field strength). In other examples, a switch position value can be an average of all or some of the sensor signals from sensor array elements at a particular point in time, and/or each sensor signal can be averaged over a particular period of time to obtain a switch position value.

In block 1106, the maximum switch position value is compared to one or more switch position thresholds, and/or the minimum switch position value is compared to one or more switch position thresholds. For example, as in examples described above, the switch position thresholds for the maximum value can include two thresholds used for three switch positions in the switch degree of freedom. Similarly, two switch position thresholds can be used for the minimum value, e.g., thresholds that are different from the thresholds used for the maximum value can be used for three switch positions in the switch degree of freedom. Additional or fewer amount of thresholds can be used in various implementations.

In some implementations, the determined maximum and minimum switch position values can be converted to digital values at discrete digital signal levels. For example, the digital switch position values can be at one of three levels based on the amplitudes of the maximum and minimum signals relative to the switch position thresholds, as described with respect to the example of FIG. 10.

In block 1108, the switch position of a first switch mechanism (e.g., switch mechanism 420) is determined based on the comparison of block 1106 using the maximum switch position value. In some examples, if the maximum value is above a first high threshold, then the switch mechanism is at the closest switch position. If the maximum value is below the first high threshold and above a first low threshold, then the switch mechanism is at a middle switch position. If the maximum value is below the first low threshold, then the switch mechanism is at a furthest switch position. Additional or fewer switch positions can be determined based on thresholds in other implementations.

In block 1110, the switch position of a second switch mechanism (e.g., switch mechanism 440) is determined based on the comparison of block 1106 using the minimum switch position value. For example, if the minimum value is below a second low threshold, then the switch mechanism is at the closest switch position. If the minimum value is above the second low threshold and below a second high threshold, then the switch mechanism is at a middle switch position. If the minimum value is above the second high threshold, then the switch mechanism is at a furthest switch position. Additional or fewer switch positions can be determined based on thresholds in other implementations.

The determined switch positions can be used to control one or more functions of the master controller and/or a controlled slave device. For example, detected particular switch positions can be used to activate commands to the slave device (e.g., apply energy to a surgical site, activate suction or irrigation, etc.), change control modes (e.g., from a controlling mode to a non-controlling mode or vice-versa), activate other functions such as user interface functions in a user interface displayed on a display screen, etc.

In block 1112, a rotational (angular) position of the handle 402 can optionally be determined based on the (raw) sensor signals received in block 1102. Block 1112 can be performed at any time after block 1102, e.g., before or in parallel to any of blocks 1104-1110. In some examples, sensor signals from all the sensor array elements 430 can be compared, or sensor signals from two or three adjacent sensor array elements 430 that output the highest (or lowest) magnitude sensor signals. The sensor signal having the highest magnitude (or lowest magnitude in some cases, such as for switch mechanism 446 as described above) can indicate the rotational position of a sensor element (e.g., element 426 or 446) by indicating that the sensor array element 430 that outputs the highest (or lowest) magnitude signal is closest in rotational position to the sensor element. In some implementations, the magnitude of the sensor signal can indicate a more precise rotational position of the sensor element over the sensing area (e.g., surface area facing the sensor element) of a particular sensor array element 430. For example, sensed amplitudes may be highest when the element 426 or 446 is at a rotational position that corresponds to the center of the sensing area of a sensor array element 430, and the sensed amplitudes may gradually reduce as the sensor element is rotated about the longitudinal axis further from that center.

In some implementations, the sensed rotational position obtained in block 1112 can be used as a check or verification to a sensed position provided by one or more other sensors that detect the rotational position of the handle 402 about the longitudinal axis 413, e.g., to determine whether the other sensors are functioning correctly. In some examples, the verification can compare sensor signals from two or three adjacent sensor array elements 430. This verification can be performed at any time using the sensor signals of block 1102. In some implementations, the verification can be performed before blocks 1104-1110. For example, if the verification determines that a sensor array element 430 is malfunctioning, the output of that sensor array element can be ignored in the determination of maximum and minimum signals and switch position in blocks 1104-1110.

The blocks described in the methods disclosed herein can be performed in a different order than shown and/or simultaneously (partially or completely) with other blocks, where appropriate. Some blocks can be performed for one portion of data and later performed again, e.g., for another portion of data. Not all of the described blocks need be performed in various implementations. In some implementations, blocks can be performed multiple times, in a different order, and/or at different times in the methods.

Figure 12:
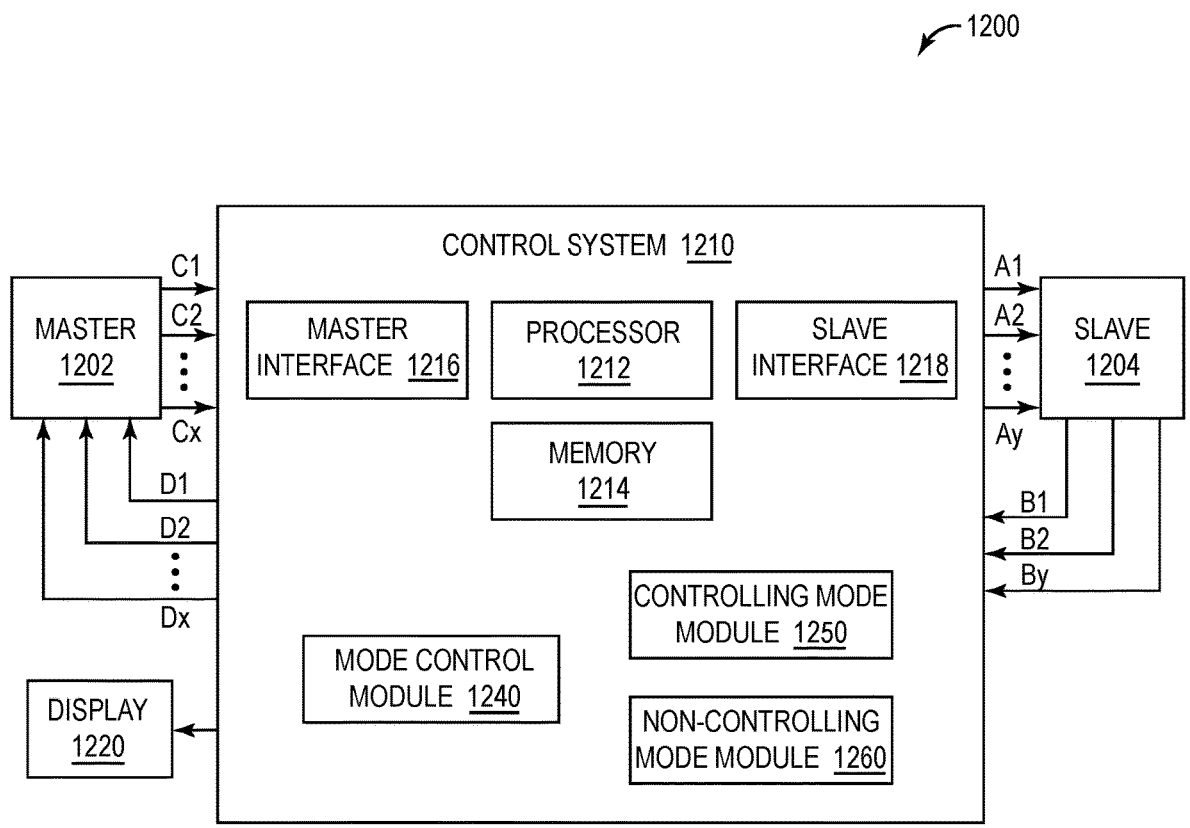
FIG. 12 is a block diagram of an example master-slave system which can be used in one or more implementations described herein.

FIG. 12 is a block diagram of an example master-slave system 1200 which can be used with one or more features described herein. System 1200 includes a master device 1202 that a user may manipulate in order to control a slave device 1204 in communication with the master device 1202. In some implementations, master device 1202 can be, or can be included in, master control workstation 102 of FIG. 1. More generally, master device 1202 can be any type of device providing a master controller that can be physically manipulated by a user. Master device 1202 generates control signals C1 to Cx indicating positions, states, and/or changes of one or more master controllers in their degrees of freedom. The master device 1202 can also generate control signals (not shown) indicating selection of physical buttons and other manipulations by the user.

A control system 1210 can be included in the master device 1202, in the slave device 1204, or in a separate device, e.g., an intermediary device between master device 1202 and slave device 1204. In some implementations, the control system 1210 can be distributed among multiple of these devices. Control system 1210 receives control signals C1 to Cx and generates actuation signals A1 to Ay, which are sent to slave device 1204. Control system 1210 can also receive sensor signals B1 to By from the slave device 1204 that indicate positions, states, and/or changes of various slave components (e.g., manipulator arm elements). Control system 1210 can include general components such as a processor 1212, memory 1214, and interface hardware 1216 and 1218 for communication with master device 1202 and slave device 1204, respectively. Processor 1212 can execute program code and control basic operations of the system 1200, including functions related to sensing the switch mechanisms described herein, and can include one or more processors of various types, including microprocessors, application specific integrated circuits (ASICs), and other electronic circuits. Memory 1214 can store instructions for execution by the processor and can include any suitable processor-readable storage medium, e.g., random access memory (RAM), read-only memory (ROM), Electrical Erasable Read-only Memory (EEPROM), Flash memory, etc. Various other input and output devices can also be coupled to the control system 1210, e.g., display(s) 1220 such as the viewer 213 of the master control workstation 102 and/or display 124 of FIG. 2.

In this example, control system 1210 includes a mode control module 1240, a controlling mode module 1250, and a non-controlling mode module 1260. Other implementations can use other modules, e.g., a force output control module, sensor input signal module, etc. In some implementations, the modules 1240, 1250, and 1260 can be implemented using the processor 1212 and memory 1214, e.g., program instructions stored in memory 1214 and/or other memory or storage devices connected to control system 1210.

Mode control module 1240 can detect when a user initiates a controlling mode and a non-controlling mode of the system, e.g., by user selection of controls, sensing a presence of a user at a master control workstation or master controller, sensing required manipulation of a master controller, etc. The mode control module can set the controlling mode or a non-controlling mode of the control system 1210 based on one or more control signals C1 to Cx.

In some implementations, controlling mode module 1250 may be used to control a controlling mode of control system 1210. Controlling mode module 1250 can receive control signals C1 to Cx and can generate actuation signals A1 to Ay that control actuators of the slave device 1204 and cause it to follow the movement of master device 1202, e.g., so that the movements of slave device 1204 correspond to a mapping of the movements of master device 1202. Controlling mode module 1250 can also be used to control forces on the master controller of the master device 1202, e.g., forces output on one or more components of the master controller, e.g., grip members, using one or more control signals D1 to Dx output to actuator(s) used to apply forces to the components, e.g., to the grip members of the master controller, in a rotary degree of freedom of the master controller, on arm links coupled to the master controller, etc. In some examples, control signals D1 to Dx can be used to provide force feedback, gravity compensation, etc.

In some implementations, a non-controlling mode module 1260 may be used to control a non-controlling mode of system 1200. In the non-controlling mode, movement in one or more degrees of freedom of master device 1202, or other manipulations of master device 1202, has no effect on the movement of one or more components of slave 1204. In some implementations, non-controlling mode can include one or more other operating modes of the control system 1210, e.g., a selection mode in which movement of the master controller in one or more of its degrees of freedom and/or selection of the control switches of the master controller (e.g., switch mechanisms 420 and 440 of FIG. 4) can control selection of displayed options, e.g., in a graphical user interface displayed by display 1220 and/or other display device. A viewing mode can allow movement of the master controller to control a display provided from cameras, or movement of cameras, that may not be included in the slave device 1204. Control signals C1 to Cx can be used by the non-controlling mode module 1260 to control such elements (e.g., cursor, views, etc.) and control signals D1 to Dx can be determined by the non-controlling mode module to cause output of forces on the master controller during such non-controlling modes, e.g., to indicate to the user interactions or events occurring during such modes.

Some implementations described herein, e.g., method 1100, can be implemented, at least in part, by computer program instructions or code which can be executed on a computer. For example, the code can be implemented by one or more digital processors (e.g., microprocessors or other processing circuitry). Instructions can be stored on a computer program product including a non-transitory computer readable medium (e.g., storage medium), where the computer readable medium can include a magnetic, optical, electromagnetic, or semiconductor storage medium including semiconductor or solid state memory, magnetic tape, a removable computer diskette, a random access memory (RAM), a read-only memory (ROM), flash memory, a rigid magnetic disk, an optical disk, a memory card, a solid-state memory drive, etc. The media may be or be included in a server or other device connected to a network such as the Internet that provides for the downloading of data and executable instructions. Alternatively, implementations can be in hardware (logic gates, etc.), or in a combination of hardware and software. Example hardware can be programmable processors (e.g. Field-Programmable Gate Array (FPGA), Complex Programmable Logic Device), general purpose processors, graphics processors, Application Specific Integrated Circuits (ASICs), and the like.

The functional blocks, operations, features, methods, devices, and systems described in the present disclosure may be integrated or divided into different combinations of systems, devices, and functional blocks.

Although the present implementations have been described in accordance with the examples shown, there can be variations to the implementations and those variations are within the spirit and scope of the present disclosure. Accordingly, many modifications may be made without departing from the spirit and scope of the appended claims.

What is claimed is:

1. A control input device comprising:
a base member;
a roll member coupled to the base member and rotatable about a central axis with respect to the base member in a roll degree of freedom;
a switch contact portion coupled to the roll member and rotatable with the roll member about the central axis in the roll degree of freedom, wherein the switch contact portion is moveable to multiple positions in a switch degree of freedom with respect to the roll member by a finger contacting the switch contact portion;
a first sensor element coupled to the switch contact portion and moveable with the switch contact portion in the switch degree of freedom and in the roll degree of freedom, wherein the first sensor element is a passive element that does not receive an electric signal; and
a base sensor element coupled to the base member and configured to sense a proximity of the first sensor element to the base sensor element, wherein the base sensor element is configured to output a signal indicative of a current position of the switch contact portion in the switch degree of freedom independently of a rotational orientation of the roll member in the roll degree of freedom.

2. The control input device of claim 1, wherein:
the switch degree of freedom is a linear degree of freedom.

3. The control input device of claim 1, wherein:
the first sensor element is a passive magnet; and
the base sensor element includes a Hall effect sensor.

4. The control input device of claim 3, wherein:
the control input device further comprises an elongated link member that extends parallel to the central axis; and
the passive magnet is coupled to the switch contact portion by the elongated link member.

5. The control input device of claim 3, wherein:
the passive magnet is a portion of a ring magnet.

6. The control input device of claim 1, wherein:
the base sensor element is arranged at least partially concentrically about the central axis.

7. The control input device of claim 1, wherein:
the signal indicative of the current position of the switch contact portion is also indicative of the rotational orientation of the roll member in the roll degree of freedom.

8. The control input device of claim 1, wherein:
the control input device further comprises a second switch contact portion coupled to the roll member and moveable in a second switch degree of freedom with respect to the roll member by a second finger contacting the second switch contact portion;
the second switch contact portion is coupled to a second sensor element moveable with the second switch contact portion in the second switch degree of freedom and in the roll degree of freedom; and
the second sensor element is a passive sensor element.

9. The control input device of claim 8, wherein:
the first sensor element includes a first magnet having a first magnetic pole facing the base sensor element;
the second sensor element includes a second magnet having a second magnetic pole facing the base sensor element; and
the second magnetic pole has a polarity that is opposite to a polarity of the first magnetic pole.

10. The control input device of claim 1, wherein:
the base sensor element includes one or more optical detectors configured to detect a beam of electromagnetic energy reflected from the first sensor element.

11. The control input device of claim 1, wherein:
the control input device further comprises a grip member, a passage in the roll member, and a shaft extending through the passage in the roll member;
the grip member is coupled to the roll member and is rotatable with the roll member about the central axis; and
the grip member is rotatably coupled to the base member by the shaft.

12. The control input device of claim 11, wherein:
the control input device further comprises an actuator;
the shaft includes a first end and a second end opposite the first end, a longitudinal axis of the shaft being defined by the first and second ends of the shaft;
the first end of the shaft is coupled to the actuator such that the actuator urges the shaft to transmit a linear force along the longitudinal axis of the shaft;
the second end of the shaft is coupled to the grip member so that the linear force causes a grip force to be applied to the grip member in a grip degree of freedom; and
the shaft is decoupled in rotation from the actuator about the longitudinal axis of the shaft.

13. A control input device comprising:
a base member;
a roll member coupled to the base member and rotatable about a central axis with respect to the base member in a roll degree of freedom, the roll member including a passage;
a shaft extending through the passage of the roll member;
a grip member coupled to the roll member and rotatable with the roll member about the central axis, the grip member being coupled to the shaft extending through the passage of the roll member;
a switch contact portion coupled to the roll member and rotatable with the roll member about the central axis in the roll degree of freedom, wherein the switch contact portion is moveable to multiple positions in a switch degree of freedom with respect to the roll member;
a first sensor element coupled to the switch contact portion and moveable with the switch contact portion in the switch degree of freedom and in the roll degree of freedom; and
a base sensor element coupled to the base member and configured to sense a proximity of the first sensor element to the base sensor element, wherein the base sensor element is arranged concentrically about the central axis, and wherein the base sensor element is configured to output a signal indicative of a current position of the switch contact portion in the switch degree of freedom independently of a rotational orientation of the roll member in the roll degree of freedom.

14. The control input device of claim 13, wherein:
the base sensor element includes a plurality of individual sensor elements arranged concentrically about the central axis;
the first sensor element is coupled to a link member having a longitudinal axis parallel to the central axis; and
the plurality of individual sensor elements are spaced concentrically about the central axis.

15. The control input device of claim 14, wherein:
at least a portion of the first sensor element is overlapping with at least one of the plurality of individual sensor elements along an axis parallel to the central axis at all orientations of the first sensor element in the roll degree of freedom.

16. The control input device of claim 14, wherein:
the base sensor element includes a substrate;
the substrate includes an aperture;
the plurality of individual sensor elements are positioned on the substrate; and
the shaft extends through the aperture in the substrate.

17. The control input device of claim 13, wherein:
the first sensor element includes one of an optical emitter or an optical detector; and
the base sensor element includes the other of the optical emitter or the optical detector.

18. A control input device comprising:
a base member;
a roll member comprising a first end, a second end opposite the first end, and a passage between the first and second ends, the roll member being rotatable in a roll degree of freedom about a central axis defined between the first and second ends;
a shaft extending through the axial passage of the roll member;
a grip member coupled to the roll member and to the shaft, the grip member being rotatable with the roll member about the central axis;
a switch contact portion coupled to the roll member, the switch contact portion being rotatable with the roll member in the roll degree of freedom, and the switch contact portion being moveable in a switch degree of freedom with respect to the roll member;
a base sensor element of a distance sensor system, the base sensor element being coupled to the base member; and
a first sensor element of the distance sensor system, the first sensor element being coupled to the switch contact portion, the first sensor element being rotatable with the roll member in the roll degree of freedom, the first sensor element being moveable with the switch contact portion in the switch degree of freedom, and the first sensor element being separated from the base sensor element by a variable distance that corresponds to positions of the switch contact portion in the switch degree of freedom.

19. The control input device of claim 18, wherein:
a signal is generated by the base sensor element;
the signal comprises a parameter; and
the parameter comprises a value that corresponds to the variable distance that corresponds to positions of the switch contact portion in the switch degree of freedom.

20. The control input device of claim 19, wherein:
the value further corresponds to a particular orientation of a plurality of orientations of the roll member about the central axis.

* * * * *

UNITED STATES PATENT AND TRADEMARK OFFICE
CERTIFICATE OF CORRECTION

PATENT NO. : 12,150,726 B2  
APPLICATION NO. : 17/269848  
DATED : November 26, 2024  
INVENTOR(S) : Luptak et al.

Page 1 of 1

It is certified that error appears in the above-identified patent and that said Letters Patent is hereby corrected as shown below:

In the Claims

In Column 35, Line 25, delete "the axial passage" and insert -- the passage -- therefor.

Signed and Sealed this  
Seventh Day of January, 2025

Derrick Brent  
*Acting Director of the United States Patent and Trademark Office*